United States Patent [19]
Swanson et al.

[11] Patent Number: 5,459,570
[45] Date of Patent: Oct. 17, 1995

[54] METHOD AND APPARATUS FOR PERFORMING OPTICAL MEASUREMENTS

[75] Inventors: Eric A. Swanson, Maynard; David Huang; James G. Fujimoto, both of Cambridge; Carmen A. Puliafito, Weston; Charles P. Lin, Somerville; Joseph S. Schuman, Boston, all of Mass.

[73] Assignee: Massachusetts Institute of Technology, Cambridge, Mass.

[21] Appl. No.: 33,194

[22] Filed: Mar. 16, 1993

Related U.S. Application Data

[63] Continuation of Ser. No. 692,877, Apr. 29, 1991, abandoned.
[51] Int. Cl.⁶ .................................................. G01D 9/02
[52] U.S. Cl. ........................... 356/345; 356/357; 356/360
[58] Field of Search ................................ 356/345, 356, 356/358, 357, 355, 359, 360; 250/227.19, 227.27

[56] References Cited

FOREIGN PATENT DOCUMENTS 8611055  5/1987  United Kingdom .

OTHER PUBLICATIONS

Youngquist & Davies, "Optical coherence–domain . . . technique", Optics Letters 12, 158–160, Mar. 1987.
Takada, Yokohama, Chida & Noda, "New measurement system . . . technique", Applied Optics 26, 1603–1606, May 1, 1987.
Danielson & Whittenberg, "Guided–wave reflectometry w/micrometer resolution", Applied Optics 26, 2836–2842, Jul. 15, 1987.
Fercher, Mengedoht & Werner, "Eye–length measurement . . . light", Optic Letters 13, 186–188, Mar. 1988.
Beaud & Salthe, "Optical reflectometry w/micrometer . . . devices", IEEE Journal of Quantum Electronics 25, 755–759, Apr. 1989.

Gilgen & Beaud, "Submillimeter optical reflectometry", Journal of Lightwave Technology 7, 1225–1233, Aug. 1989.
Tateda & Horiguchi, "Water penetration sensing using . . . OTDR", IEEE Photonics Technology Letters 3, 1–3, Jan. 1991.
Hitzenberger, "Optical measurement of the axil . . . interferometry" Investigate Ophthal. & Visual Science 32, 616–624, Mar. 1991.
Kobayashi & Noda, "Polarization–independent . . . reflectometer", Journal of Lightwave Technology 9, 623–628, May 1991.
Kobayashi & Noda, "Optical fiber component . . . reflectometer", IEEE Photonics Technology Letters 3, 564–566, Jun. 1991.
Takada & Noda, "Reyleigh backscattering . . . spatial resolution", Applied Physics Letters 59, 143–145, Jul. 8, 1991.

(List continued on next page.)

Primary Examiner—Samuel A. Turner
Attorney, Agent, or Firm—Wolf, Greenfield & Sacks

[57] ABSTRACT

A method and apparatus for performing various optical measurements is provided utilizing an optical coherence domain refrectometer (OCDR). A short coherence optical radiation source applies optical radiation through like optical paths to a sample and an optical reflector. The optical reflector is movable in accordance with a predetermined velocity profile to permit interferometric scanning of the sample, the resulting output having a Doppler shift frequency modulation. This output may be demodulated and detected to obtain desired measurements and other information. Additional information may be obtained by applying radiation from two or more sources at different wavelengths to the sample and reflector and by separately demodulating the resulting outputs before processing. Birefringent information may be obtained by polarizing the optical radiation used, by suitably modifying the polarization in the sample and reference paths and by dividing the output into orthogonal polarization outputs which are separately demodulated before processing.

51 Claims, 6 Drawing Sheets

OTHER PUBLICATIONS

Takada & Yukimatsu, "Resolution control of low . . . 14 and 290", IEEE Photonics Technology Letter 3, 676–678, Jul. 1991.

Huang & Fujimoto, "Micron–resolution ranging . . . reflectometry", Lasers in Surgery and Medicine 11, 419–425, 1991.

Takada, Himeno & Yukimatsu, "Phase–noise . . . reflectometry", Applied Physics Letters 59, 2483–2486, Nov. 11, 1991.

Huang & Fujimoto, "Optical coherence tomography", Science 254, 1178–1181, Nov. 22, 1991.

Clivaz & Gilgen, "High–resolution reflectometry . . . tissues", Optics Letters 17, 4–6, Jan. 1, 1992.

Sorin & Gray, "Simultaneous thickness and . . . reflectometry", IEEE Photonics Technology Letters 4, 105–107, Jan. 1992.

Swanson & Puliafito, "High–speed optical . . . reflectometry", Optics Letters 17, 151–153, Jan. 15, 1992.

Hitzenberger & Fercher, "Measurement of corneal . . . inferometry", Investigative Opthal. & Visual Science 33, 98–103, Jan. 1992.

Kobayashi & Noda, "Polarization–independent . . . inferometry", Journal of Lightwave Technology 9, 0733–8724, May. 1991.

METHOD AND APPARATUS FOR PERFORMING OPTICAL MEASUREMENTS

This application is a continuation of application Ser. No. 07/692,877 filed on Apr. 29, 1991, now abandoned.

FIELD OF THE INVENTION

This invention relates to the performing of precision measurements and more particularly to a method and apparatus for optically performing precision measurements, generally distance and thickness measurements, on biological and other samples.

BACKGROUND OF THE INVENTION

There are many industrial, medical, and other applications where high resolution (generally less than 10 micrometer) measurement of distances, thicknesses, and optical properties of a biological or other sample are required. These applications include measurements of biological tissue layers, semiconductors and other applications involving multiple thin layers of material, as well as in the non-destuctive testing of small structures such as integrated optical circuits, optical connectors, optical couplers, semiconductor lasers and semiconductor optical amplifiers. Such applications also include various medical applications including laser microsurgery and diagnostic instrumentation.

Existing techniques for performing such measurements include optical coherence domain reflectometers (OCDR), optical time domain reflectomerry (OTDR), ultrasound, scanning laser microscopes, scanning confocal microscopes, scanning laser ophthalmoscopes and optical triangulation. Existing OCDR systems do not normally have the rapid data acquisition rate required for the measurement of biological or other samples having the potential for dynamic movement; while OTDR systems are very expensive and have only limited resolution and dynamic range.

Ultrasound, which is perhaps the most commonly used technique, is disadvantageous for applications such as taking measurements on the eye in that, in order to achieve the required acoustic impedance matches, and to thus avoid beam losses and distortion, contact is generally required between the ultrasonic head or probe and the product or patient being scanned. While such contact is not a problem when scans are being performed on, for example, a patient's chest, such probes can cause severe discomfort to a patient when used for taking eye measurements such as those used for measuring intraocular distances for computing the power of lens implants.

The relatively long wavelengths employed in ultrasound also limit spatial resolution. Further, ultrasound depends on varying ultrasound reflection and absorption characteristics to differentiate and permit recording or display of tissue, or other boundaries of interest. Therefore, when the acoustic characteristics of adjacent layers to be measured are not significantly different, ultrasound may have difficulty recognizing such boundaries.

Scanning laser or confocal microscopes and scanning laser ophthalmoscopes (SLO) provide highly spatially resolved images, for example being able to generate real time video images of the eye with a lateral resolution of a few micrometers. However, the depth resolution of SLO's quickly degrade with decreasing numerical aperture. For example, SLO measurements of the retina through the pupil aperture restrict the depth resolution to roughly 200 microns. SLO's are also expensive, costing in the range of a quarter million dollars.

Optical triangulation offers fairly high resolution, but requires parallel boundaries. Such devices also have relatively poor signal-to-noise ratios and have degraded resolution at greater depths, where numerical aperature is restricted.

A need, therefore, exists for an improved method and apparatus for performing high resolution measurements and in particular for optically performing such measurements, which improved technique does not require contact with the body being measured, which maintains substantially constant high resolution over a scanning depth of interest, regardless of available aperture size and which is relatively compact and inexpensive to manufacture. Such a system should also be capable of providing differentiation between sample layers, should be able to provide identification of layer material or of selected properties thereof, should be able to provide one, two and three-dimensional images of a scanned body and should be rapid enough for use in biological and other applications where the sample being measured changes over relatively short time intervals. Finally, it would be desirable if such technique could also provide information concerning the birefringence property and spectral properties of the sample.

SUMMARY OF THE INVENTION

In accordance with the above, this invention utilizes an optical coherence domain reflectometer (OCDR) technique to perform various measurements. In particular, optical measurements are performed on a sample by providing a short coherent length optical radiation source at a wavelength $\lambda$ and a reference optical reflector. The short coherence length permits fine spatial resolutions. The optical source could, for example, be a light emitting diode or super luminescent diode and would preferably have a coherence length of less than 10 micrometers. The reference optical reflector would typically be a high reflection mirror. First and second optical paths are provided leading to the reference reflector and sample, respectively. Optical radiation (i.e. light) from the source is split, being applied through the first optical path to the reflector and through the second optical path to the sample. Changes are made in the length of the first optical path with a predetermined velocity profile, for example at a uniform velocity V. Reflections from the reflector received through the first optical path and reflections from the sample received through the second optical path are optically combined, the resulting combined optical output having interference fringes at matched path lengths and forming the envelope for a modulating signal. The modulated signal may be modulated at the Doppler shift frequency $f_D = 2V/\lambda$ caused by reflector translation or may be a combination of $f_D$ and a modulating frequency $f_M$. The combined optical output is then demodulated to obtain the coherence envelope and the demodulated output processed to obtain information concerning the selected measurements. A logrithmic amplifier may be provided in the demodulator for dynamic range compression.

The velocity V at which changes in the path length are made is preferably relatively high, being greater than approximately 1 cm/sec for the preferred embodiment. To avoid the need for a superimposed modulating frequency $f_M$, the reflector translation velocity should be high enough so that $f_D$ is higher than the predominant low frequency noise. For the preferred embodiment, the changes in first path length may be ramped, with the change in one direction occurring at the velocity V and the change in the other direction occurring much more rapidly. The changes in first path length may also have a triangular pattern, with the change in at least one direction being at the velocity V. The scan pattern may also be a sinusoidal pattern. With uniform velocity, measurements would be taken during a translation which occurs at the velocity V and may occur for path length changes in both directions with a triangular drive. With a sinusoidal drive, the nonlinearity may be detected and taken into account in subsequent processing.

The system is preferably implemented utilizing optical fibers in the optical paths; however, the system may also be implemented utilizing bulk optics or other optical components. Where optical fibers are employed, the lengths of the paths and the lengths of the fibers in the paths are preferably both substantially equal.

The changes in the first optical path are preferably accomplished by reciprocating the mirror or other reference reflector in a direction substantially perpendicular to the optical path. A suitable means may be provided for maintaining the reflector in alignment in spite of movement and wobble of the reflector as it is moved. The numerical aperture for the coupling to the sample should also correspond to a depth field equal to a predetermined depthsextent within the sample over which measurements are to be taken.

If measurements are desired on at least one birefringent layer, the system includes a means for polarizing the optical energy from the source in a selected first direction, the polarization of the light being altered differently for energy applied to the reflector and to the sample. The elements which alter the polarization also cause reflected light energy from the reflector to be polarized in a second selected direction and cause reflected light energy from the sample to be polarized in a direction dependent on the birefrigence of the birefringent sample. The combined outputs containing interferometric fringes are split and detected as two outputs having orthogonal polarizations. These two outputs are then separately processed to obtain separate interferometric signals and the separate interferometric signals are combined to provide selected indications of birefringence.

In order to enhance the ability of the system to distinguish a boundary between layers having similar optical properties, and to obtain other information concerning such layers, advantage is taken of the fact that the optical absorption, impedance, and other optical characteristics of materials may vary with wavelength. Thus, one layer of a junction may be more easily detected at a first wavelength of the optical energy, while another layer may be more easily detected at a different wavelength. For one embodiment of the invention, two or more short coherence length optical sources provide optical radiation at different wavelengths, for example $\lambda 1$ and $\lambda 2$, the sample reacting differently to inputs received at these different wavelengths. This results in a first interferometric optical output modulated at a frequency $f_{D1}=2V/\lambda 1$ and a second interferometrical optical output modulated at a frequency $f_{D2}=2V/\lambda_2$. The two outputs are separately demodulated and may then be separately processed or processed together.

The sample arm may terminate in a probe which may be used for one dimensional measurement on a sample, or may be scanned to obtain two or three dimensional measurements. The probe may be utilized to map or perform measurements on the eye, skin or other externally accessible body part, or may be incorporated into an endoscope for probing internal body cavities such as blood vessels, airways and digestive tract.

The foregoing and other objects, features and advantages of the invention will be apparent from the following more particular description of preferred embodiments of the invention as illustrated in the accompanying drawings.

IN THE DRAWINGS

DETAILED DESCRIPTION

Figure 1:
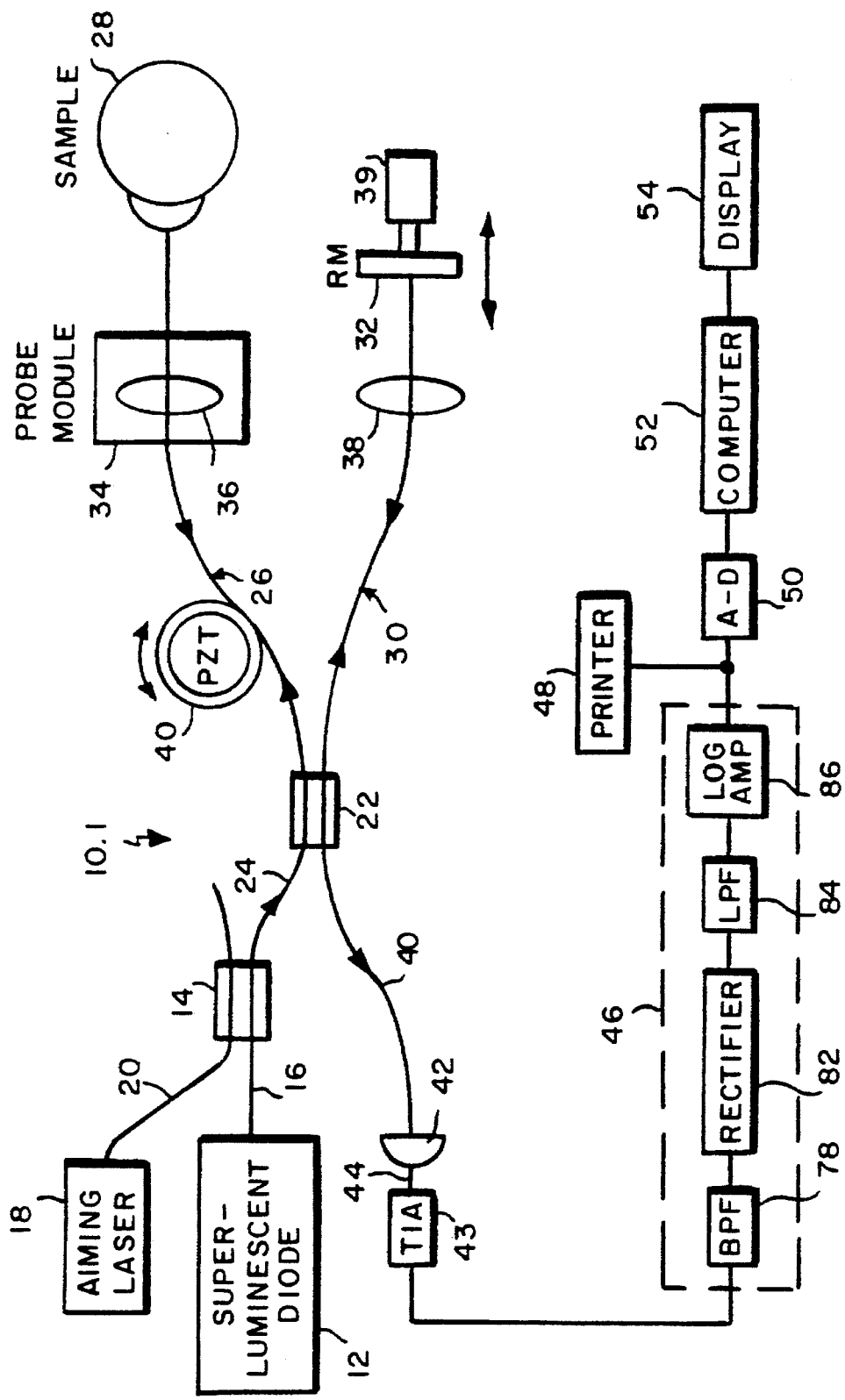
FIG. 1 is a schematic block diagram of a first fiber optic embodiment of the invention.

Referring first to FIG. 1, a fiber optic optical coherence domain refrectometer (OCDR) 10.1 is shown which incorporates the teachings of this invention. In particular, the output from a short coherence length optical source 12 is coupled as one input to an optical coupler 14. Such coupling may be through a fiber optic path 16. Source 12 may, for example, be a light emitting diode (LED) or super luminescent diode (SLD) of suitable wavelength, and preferably has a coherence length of less than 10 micrometers. Source 12 might also be a pulsed laser source or an incandescent source; but for most applications a LED or SLD would be preferable, a pulsed laser having higher power but being much more costly and having lower resolution, and an incandescent source having good resolution but very low power. As will be discussed later, it is desirable that the coherence length of source 12 be minimized to enhance the resolution of the system. The other input to coupler 14 is from a laser 18 generating an optically visible output which is applied to the coupler through a fiber optic path 20. As will be discussed in greater detail later, laser 18 does not contribute to the normal operation of the system and is utilized only to provide a source of visible light for proper alignment with a sample when the light from source 12 is in the infrared region or is otherwise not visible. Further, unless otherwise indicated, all optical fibers utilized for the various embodiments will be assumed to be single mode fibers. These fibers may be polarization maintaining or not, but are preferably polarization maintaining to insure good polarization mode matching.

The output from coupler 14 is applied as the input to coupler 22 through fiber optic path 24. The light or optical energy received at coupler 22 is split between a first fiber optic path 26 leading to sample 28 being scanned and a second fiber optic path 30 leading to a reference reflector or mirror 32. Fiber optic path 26 is terminated in a probe module 34 which includes a lens 36 for focussing the energy beam applied to the module on sample 28 and for receiving reflections from sample 28 and transmitting the reflections back to the fiber. Path 30 also has a focussing lens 38 for focussing light on mirror 32. The optical fibers of path 26 may be wrapped around a piezoelectric crystal 40 which vibrates (i.e. expands and contracts) in response to an applied electrical signal to cause slight expansion and contraction of the optical fiber and to thus modulate the optical signal passing through the fiber. The total length of path 26 between coupler 22 and a selected depth point in sample 28 and the total length of path 30 between coupler 22 and mirror 32 should be substantially equal for each depth point of the sample during a scan of selected depth range. In addition, to prevent group velocity dispersion which would decrease spatial resolution, the lengths of the optical fibers in paths 26 and 30 should also be substantially equal. Alternatively, the group velocity dispersions may be equalized by placing optical materials of known group velocity dispersion and thickness in the light paths to compensate for any inequality. For example, where the fiber in the reference path may need to be shorter than that in the sample probe, a length of high dispersion material may be included in the reference path. It is also important that the termination of the optical fibers utilized in the system be angle polished and/or anti-reflection coated to minimize reflections.

Reference mirror 32 is secured to a mechanism 39 which reciprocates the mirror toward and away from lens 38 in a particular pattern. For the embodiment shown in FIG. 1, mechanism 39 moves mirror 32 away from lens 38 at a uniform, relatively high velocity, which velocity is preferably greater than 1 cm/sec. The length or extent or movement of mirror 32 by mechanism 39 is at least slightly greater than the desired scan depth range in sample 28. When mirror 32 reaches the far end of its travel path, for one embodiment the mirror is rapidly returned to the initial position, the scan having a generally ramp or sawtooth profile, with measurements being taken on the ramp. Mechanism 39 may also return mirror 32 to its initial position at substantially the same rate V, movements of the mirror thus being in a triangular pattern. With a triangular scan, readings or measurements can be taken with the mirror moving in either one of the two directions, or can be taken with the mirror moving in both directions. Mechanism 39 may be any one of a variety of devices adapted for performing the mirror translation function. For example, mechanism 39 could be a stepper motor, the motion of which is applied to mirror 32 through an averaging mechanism to provide uniform velocity. A DC servo motor might also be utilized to obtain the desired motion. Various electromagnetic actuators, for example, a speaker coil, may also be utilized for moving the mirror. With such electromagnetic actuators, detection of mirror position and servocontrol thereof are also required in order to achieve the desired uniform motion. More specifically, in such a system a signal indicative of desired mirror position at each point in the mirror travel path would be compared against a signal from a detector of actual mirror position and any resulting error signals utilized to control the actuator to maintain the mirror moving at the desired constant velocity. It would also be possible to use a servo-controlled galvanometer driven linear translator for the mechanism 39.

One potential problem is that when the mirror 32 is being translated at high speed by mechanism 39, it is virtually impossible to eliminate some wobbling of the mirror which may adversely affect the accuracy of distance determinations. Various mechanisms may be utilized to correct for such mirror wobble so that a beam reflected from the mirror will be coupled back into the fiber. One simple technique to compensate for the wobble problem is to have lens 38 focus the beam at a small spot near the center of mirror 32 rather than causing the lens to apply a collimated beam to the mirror. The focussed beam provides greater tolerance in returning the beam to the fiber in spite of slight angular variations in the mirror than does a collimated beam.

A second technique to compensate for mirror wobble is to substitute a corner-cube on which the beam is initially incident for mirror 32. Reflections from the corner-cube reflect off a stationary mirror and the corner-cube to the fiber. Corner-cubes generally have the property that, regardless of the angle at which a beam is incidentthereon, the beam will always return in exactly the opposition direction at which the beam was incident.

Reflections received by probe 34 from sample 28 are applied through path 26 to coupler 22 and optical reflections from mirror 32 are applied through lens 38 and path 30 to the coupler. The optical signals received from the sample and the reference are combined in coupler 22, resulting in interference fringes for length matched reflections, (i.e. reflections for which the difference in reflection path lengths is less than the source coherence length) and the resulting combined output is coupled onto fiber optic path 40. The optical signal on fiber path 40 is applied to a photodetector 42 which converts the optical combined signal on path 40 to a corresponding current-varying electrical signal. The current-varying electrical signal on output line 44 from photodetector 42 is preferably convertd to a voltage varying signal by a transimpedance amplifier (TIA) 45 or other suitable means, the TIA output being applied as an input to a demodulator 46.

Various forms of demodulation may be utilized in practicing the teachings of this invention. In its simplest form, demodulator 46 may consist of a bandpass filter 78 centered around the modulation frequency of the combined output signal and an envelope detector. The filter assures that only the signal of interest is looked at and removes noise from the output. This enhances the signal-to-noise ratio of the system and thus system sensitivity. The filtered signal is then applied to the envelope detector.

The envelope detector in demodulator 46 may consists of a rectifier 82 and a subsequent low pass filter 84. The rectifier output would be proportional to the square root of the sample reflectivity. The second filter removes any high frequency components from what is basically a base band signal. The demodulator preferably also includes a logrithmic amplifier 86, either before or after the rectifier, for dynamic range compression. Without the logrithmic amplifier, strong reflections from boundaries would either be off scale or weaker reflections would not be visible.

The exemplary demodulator described above is one type of heterodyne demodulator. However, a variety of other demodulation techniques known in the art may also be utilized to perform the demodulator function.

The demodulated output from circuit 46 is the interferometric envelope signal of interest. A suitable printer 48 may be utilized to obtain a visual record of this analog signal which may be utilized by a doctor, engineer or other person for various purposes. For preferred embodiments, the analog output from demodulator 46 is applied, either in addition to or instead of to printer 48, through an analog-to-digital converter 50 to a suitable computer 52 which is programmed to perform desired analyses thereon. Computer 52 may, for example, control the display of the demodulated signal on a suitable display device 54, such as a cathode ray tube monitor, or may control a suitable printer to generate a digital record. In addition, computer 52 may detect various points of interest in the demodulated envelope signal and may perform measurements or make other useful determinations based on such detections. Computer 52 may be a suitably programmed standard processor or a special purpose processor may be provided for performing some or all of the required functions.

The embodiment shown in FIG. 1 would be utilized where mirror 32 is scanned by mechanism 39 at an intermediate but uniform velocity. For purposes of this discussion, an intermediate scanning velocity is considered one at which the Doppler frequency shift caused by the mirror movement is not negligible, but is low enough to fall within the predominant low frequency noise for the system. The noise spectrum includes noises arising from fluctuations in light source 12, mechanical components and electrical circuits, and are larger at lower frequencies, typically below 10 kHz. The Doppler shift frequency $f_D$ results from the translation of the reference mirror 32 and is given by the equation:

$$f_D = 2V/\lambda$$

where V is the velocity at which the mirror is being moved at the given time and $\lambda$ is the optical wavelength of the source. Thus, where this Doppler shift is less than 10 kHz, additional modulation is needed to shift the modulation frequency above the predominant noise spectrum. In FIG. 1, this is achieved by introducing sinusoidal phase modulation by use of piezoelectric transducer 40. While in FIG. 1 the additional modulation is introduced by use of the oscillator or transducer in reference path 26, such modulation could also be provided in the sample arm or path 30. Further, in addition to piezoelectric, the small movement required for this supplemental modulation may be achieved using electromagnetic, electrostatic, or other elements known in the art for providing small generally sinewave movements. Alternatively, this supplemental modulation can be achieved by passing light in the reference arm and/or sample arm through acousto-optic modulators. Such modulators would normally be attached to provide supplemental movement to the mirror.

The supplemental modulation from transducer 40 or other suitable means which modulate the optical path length is at a frequency $f_M$ and the oscillation-amplitude of this modulator is adjusted so that the peak-to-peak oscillating movement or optical delay change is one-half of the wavelength $\lambda$ of source 12. The combined effect of the supplemental modulation and the Doppler shift frequency causes the output envelope to be on modulating frequencies of $f_D$, $f_M + f_D$, $f_M - f_D$ and at higher harmonics and $f_M \pm f_D$. $f_M$ is normally chosen to be higher than the predominant noise spectrum.

Demodulation of the output from photodetector 42 is normally at $f_M + f_D$ and/or $f_M - f_D$. For purposes of illustration, it will be assumed that demodulation is at $f_M + f_D$. The center frequency for bandpass filter 78 is thus set for the frequency $(f_M + f_D)$. The bandwidth for filter 78 should be approximately two to three times the full-width-half-maximum (FWHM) bandwidth of the received signal to avoid signal broadening and distortion. This bandwidth is given by the equation $$\Delta f = \frac{4(\ln 2)V}{\pi \Delta l} \sim \frac{V}{\Delta l}$$

where V is the velocity at which the mirror is being moved, $\Delta l$ is the coherence length of source 12 and is given by the equation $$\Delta l = (\ln 2)\frac{2}{\pi}\frac{\lambda^2}{\Delta \lambda}$$

where $\Delta \lambda$ is the full-width half-power spectral width or wavelength bandwidth of the optical radiation or light from source 12 and might typically be in a range from 20 to 30 nm. The bandwidth of low pass filter 84 would typically be roughly identical to that of bandpass filter 78.

If the velocity at which mirror 32 is being moved has a high enough speed so that the resulting Doppler shift frequency is higher than the predominant noise spectrum, then supplemental modulation by a device such as phase modulator 40 is not required. For an 830 nm wavelength output from source 12, which might be a typical source wavelength, this occurs for a scan velocity above approximately 4 mm/sec. In such a system, the detection electronics would be the same as those discussed above in conjunction with FIG. 1 except that the center frequency for bandpass filter 78 would be set to the Doppler shift frequency $f_D$. As the scanning speed increases, the bandwidth of the signal $\Delta f$ also increases, resulting in corresponding increases in the bandwidth of filters 78 and 84. This leads to a loss of detection sensitivity, an inevitable result of high speed scan.

High speed scans also permit measurements for most samples to be completed in less than a second, a time frame which is consistent with the performance of biological measurements.

For the embodiments discussed to this point, the scanning of mirror 32 has been at constant velocity, at least through the scan interval. However, for very high speed scanning at high scan repetition rates that cannot be realized with servo-controlled constant velocity mechanical drives, resonantly (sinusoidal) driven mechanical actuators can be used to drive mirror 32. These actuators can be galvanometrically or electrodynamically driven at the resonant frequencies of the mechanical actuator system and are commercially available.

However, when the actuator 39 has a sinusoidal velocity profile, the Doppler shift frequency $f_D$ is no longer constant, and the demodulator 46 must be adapted for this carrier frequency variation. There are least two methods for accomplishing this objective. In both cases, as illustrated for system 10.2 in FIG. 2, an output line 87 is provided from a position sensor in the actuator 39. The voltage on line 87 will normally vary as a function of actuator position and thus of position for mirror 32; however, the position sensor output may also be current varying. If the sensor provides a digital output, then line 87 may be connected to computer 52 without going through A/D converter 50'. The signal on line 87 is required when actuator 39 has a non-linear velocity profile so that intensity and other inputs received at computer 52 may be correlated with scan position in the sample. This correleation is not required with a linear scan where position can be determined from the time an input is received.

In the simpler technique, the acceptance band for bandpass filter 78 and low pass filter 84 are increased to accommodate the variations in the Doppler shift frequency $f_D$ over a large portion of the sinusoidal motion of mirror 32. These variations occur because $f_D$ varies directly with variations in V. This increased demodulator acceptance bandwidth will lead to increased acceptance of noise and thus results in lower detection sensitivity. However, this technique is simple and can be used in cases where the requirement for detection sensitivity is not critical. Further, this increase in acceptance bandwidth may be relatively small when the signal bandwidth $\Delta f_{FWHM}$ is already large relative to $f_D$, this occurring when the coherent length is very small.

Figure 2:
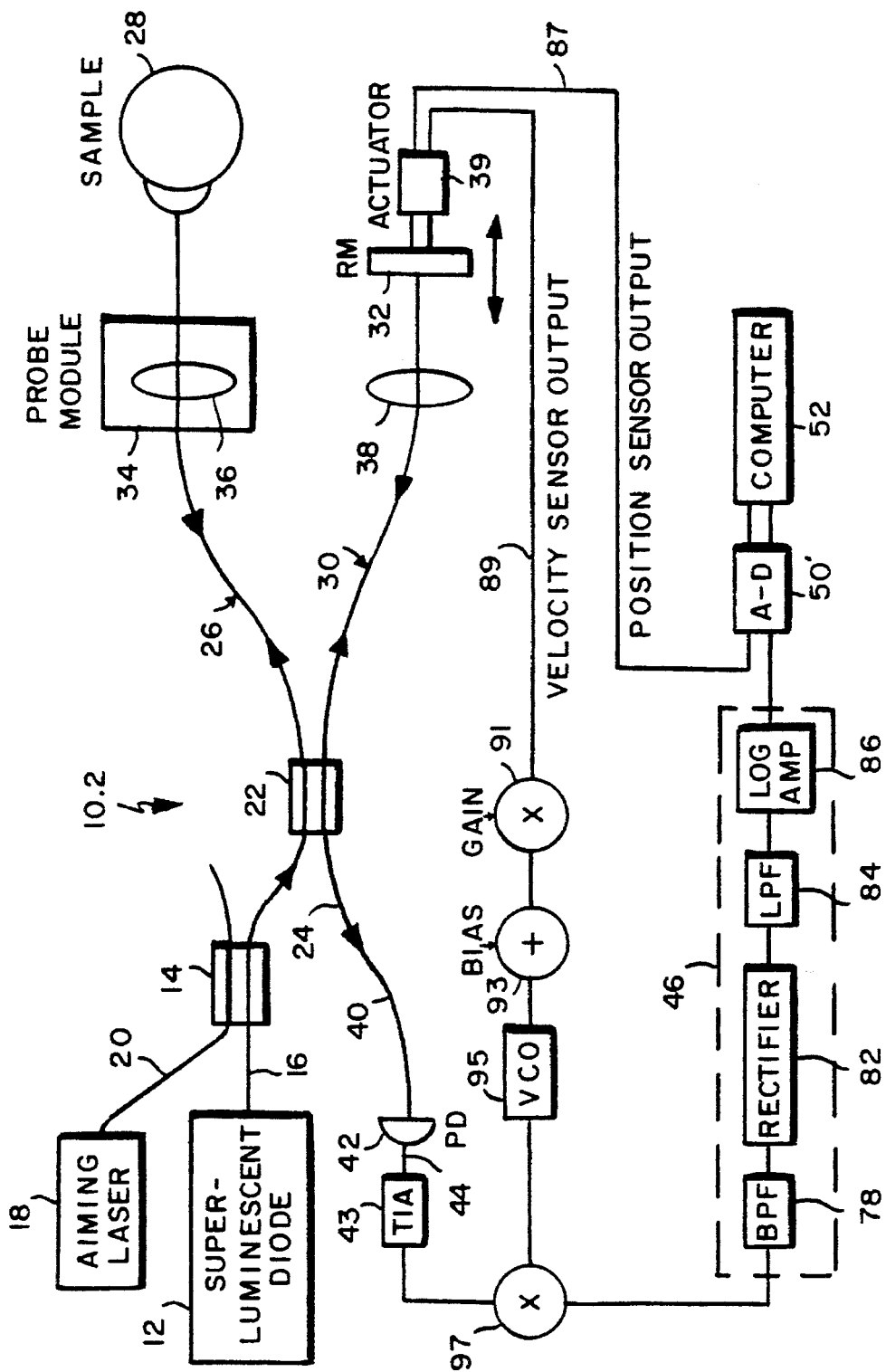
FIG. 2 is a schematic block diagram of a second fiber optic embodiment of the invention.

FIG. 2 illustrates the second technique wherein the demodulation frequency is dynamically tuned to the instantaneous Doppler shift frequency using a superhetrodyne system. A sensor at actuator or drive mechanism 39 provides a velocity dependent voltage on line 89 which is modified by a gain circuit 91 and a bias circuit 93 before being applied to a voltage controlled oscillator 95. The output from oscillator 95 is multiplied in a circuit 97 with the output from detector 42 via amplifier 43. The gain and bias of the signal applied to VCO 95 are adjusted so that the modulating frequency at the output from multiplier 97 is substantially constant at a desired center frequency which is selected as the center frequency for bandpass filter 78. As with the embodiment of FIG. 1, the bandwidth of filter 78 is set at two to three times the peak signal bandwidth and, except for the need for the position sensor output on line 87, the remainder of the detection and processing would be substantially identical to that previously described in conjunction with FIG. 1.

Figure 3:
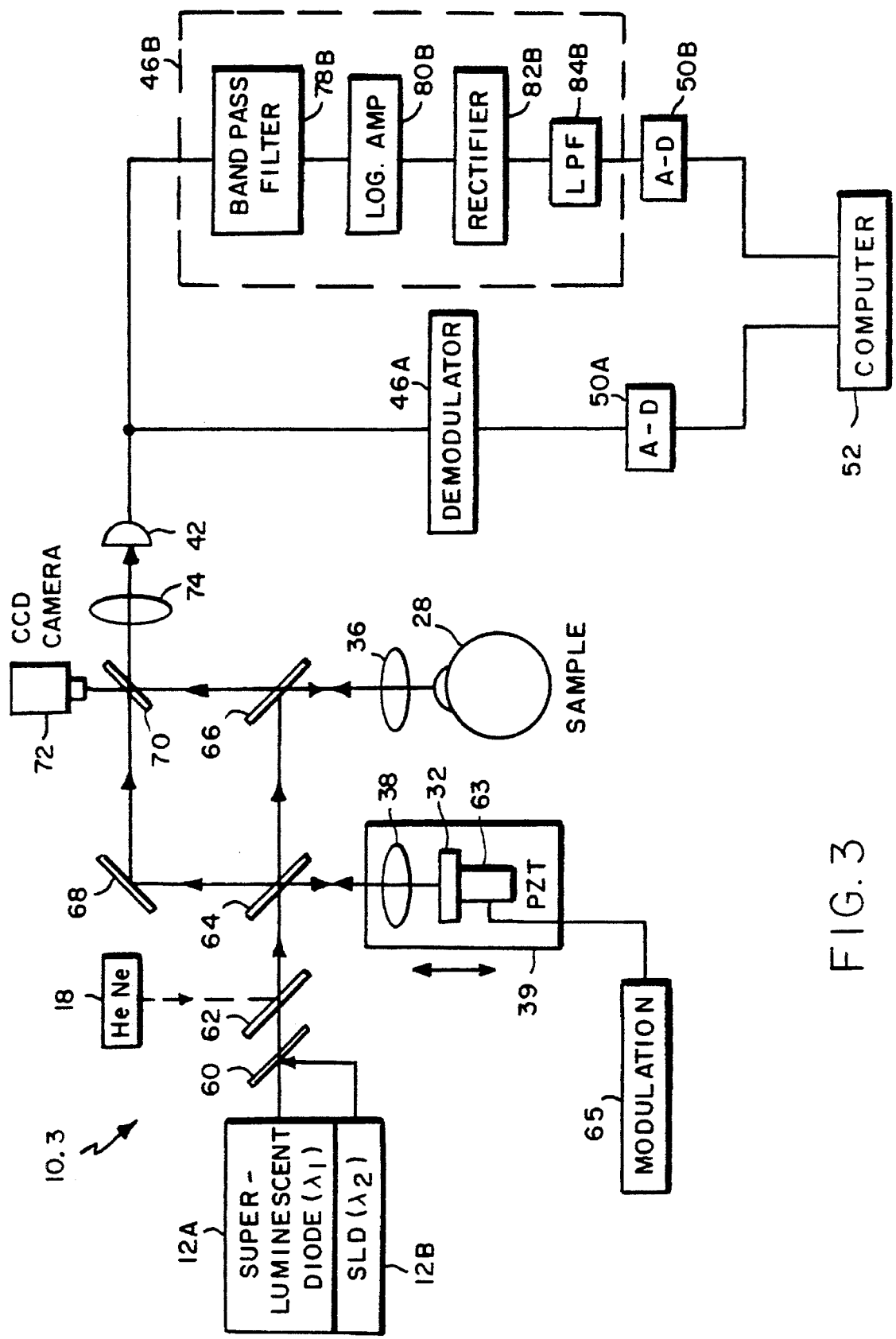
FIG. 3 is a schematic block diagram of a bulk optic embodiment of the invention illustrating the use of two separate wavelengths to enhance resolution.

FIG. 3 shows a system 10.3 which is similar to that of FIG. 1, except that bulk optics are utilized rather than fiber optics and ability to observe spatial properties is enhanced by providing two light sources 12A and 12B which are at different wavelengths. While the multiple wavelength option is being shown for purposes of illustration in conjunction with a bulk optics embodiment, it is to be understood that multiple wavelengths could also be, and may preferably be, used with the fiber optic embodiments. Sources 12A and 12B could be the same type of light sources designed to operate at different wavelengths or could be different types of light sources. The outputs from sources 12A and 12B are merged in a coupler 60, the optical output from which is applied to a coupler 62. The other input to coupler 62 is the output from a laser 18, for example, a helium neon laser, which again is used only for alignment purposes. Couplers 60 and 62 could, for example, be dichoric beam splitters, polarization beam splitters or normal beam splitters.

The output from coupler 62 is applied to beam splitters 64 and 66. Beam splitter 64 applies a portion of its input through lens 38 to mirror 32 and also passes optical radiation to beam splitter 66 which applies this radiation through lens 36 to sample 28. Reflections from mirror 32 are applied through lens 38, beam splitter 64 and mirror 68 to interferometric coupler 70. Mirror 32 and lens 38 may be part of a translation stage which is moved by a mechanism such as the mechanism 39 discussed in conjunction with FIG. 1. As was dicussed above, if such translation is being performed at a speed such that $f_D$ is below the predominant noise spectrum, it may also be necessary to, for example, mount mirror 32 to a piezoelectric crystal 63 which is vibrated under control of a modulator 65. Other methods for accomplishing this are discussed earlier. Reflections from sample 28 are applied through lens 36 and beam splitter 66 to the interferometric coupler 70.

The output from coupler 70 may be applied to a CCD camera 72 used for alignment purposes and also applied through a lens 74 to a photodetector 42. The output from the detector is applied through two separate paths. Each path contains a demodulator 46a, 46b containing a bandpass filter 78 having a center frequency which corresponds to the Doppler shift frequency $f_D$ for the given source 12 since $f_D$ varyies inversely as a function of the source wavelength, each demodulator only demodulates signals corresponding to the appropriate source wavelength permitting outputs resulting from the two source wavelengths to be separated. After being applied through corresponding A–D converters 50, the two outputs are applied to computer 52 where they may be appropriately processed.

Alternatively, a detector 42 may be provided corresponding to each source wavelength where each photodetector is preceded by an optical wavelength filter that only transmits the appropriate wavelength with an appropriate pass band. A beam splitter would be provided ahead of the optical wavelength filters, with a demodulator at the detector output.

While in FIG. 3, and in the discussion above, only two separate signals λ have been shown, this is not a limitation on the invention, and a greater number of light sources and detectors (and/or demodulator circuits) may be provided for appropriate applications.

For purposes of describing the operation of the system 10.1 or 10.3, it will be assumed that the sample 28 is the eye of a human or animal patient. When such measurements are to be made, there are three alignments which are critical. First, the beam must be aligned with the sample so that it enters the sample at a desired angle. This angle is normally an angle perpendicular to the angle of the eye layers. Second, the beam must be laterally positioned on the sample area of interest. This is a control of the lateral position of the beam. Finally, the beam must be focussed at the level of interest in the eye. A number of techniques may be utilized for performing each of these alignment functions.

In particular, a number of different techniques may be utilized to obtain a desired incidence angle. Since reflections will generally be substantially maximized when the beam is normal to the layer or surfaces being reflected off of, one simple way to achieve alignment is to adjust the position or angle of the probe of beam splitter 66, or lens 36 and/or of the sample (i.e., the patient's eye) and, with the reference arm blocked, detect reflections from the sample. The alignment at which the power of the detected reflections is maximum would thus be the desired alignment angle. It would normally be possible to locate the desired angle relatively quickly using this technique.

A second technique for achieving angular alignment is similar to the first except that the reference arm is not blocked and, with normal readings being taken from the system, alignment is manually adjusted until an alignment which maximizes the output is obtained.

A third method is to look at the direction in which the beam is reflected in order to detect beam alignment. Since it is hard to do this directly, particularly when a fiber is utilized, such determination is generally made by providing a beam splitter which directs a portion of the beam reflected from the sample to a device such as CCD camera 72 (FIG. 3) which can measure beam position. This device is initially calibrated with the system so that the spot on which the beam impinges on the camera when the beam is properly aligned with a sample is determined. Then, in operation, the sample and probe can be adjusted until an angle of alignment is achieved where the beam impinges on the CCD camera at the previously determined point.

Lateral position alignment is at this time best performed manually. To perform this operation, laser 18 is turned on. Source 12 may either be on or off for this operation. Laser 18 provides a narrow beam visual indication of the lateral position on the eye where the beam is striking and the position of either the probe beam or the patient may then be manually adjusted until the beam is striking the desired position. If light from source 12 is in a visible band, laser 18 may not be required and light from source 12 may be used for alignment.

The focussing cone angle to be utilized for performing readings is determined by balancing the desirability of having as large a numerical aperture (cone angle) as possible against being able to achieve a desired longitudinal range or depth of field in which back scattered or reflected light is efficiently coupled back to the fiber (or to the other optical path 26 where a fiber is not employed). A large numerical aperture makes angular alignment for normal incidence on the sample surface less critical and for measurement of back scattering where the returned radiation is spread over wide solid angles, a wider cone angle increases the coupling into the fiber. However, the large cone angle reduces the longitudinal range. Thus, the numerical aperture or f number should be selected to correspond to a depth of field that is equal to the longitudinal extent of the area in the eye or other sample on which measurements are to be taken. For purposes of this discussion, depth of field is defined as the longitudinal distance from the focal plane at which the back coupling efficiency into the fiber is reduced by one-half.

As for the other alignments, the sample and/or probe are moved relative to each other until the system is focussed to a desired point within the sample, i.e., within the eye. Since even with the laser it may be difficult to visually determine the focal point, a preferable way to perform focussing may be to operate the system with, for example, an output being obtained on display 54. As will be discussed later, certain high amplitude points in such output are indicative of a particular layer or transition in the eye and focus can be adjusted until this transition occurs at a desired point in the scan.

Once alignment has been achieved, the system may be utilized to take desired measurements. To perform such measurements, aiming laser 18 is turned off and source 12 is turned on. Mechanism 39 is also turned on, if not already on, to cause desired movement of the mirror. If mechanism 39 is not moving at sufficiently high velocity, it may also be necessary to turn on piezoelectric modulator 40 or 63. However, for preferred embodiments, such modulation is not required.

As previously indicated, source 12 should have a low coherence length while implies being spectrally wide. Thus, for light sources of the type previously mentioned having a coherence length of approximately 10 micrometers, spatial separation, and thus resolution, to 10 micrometers can be obtained. This is a far higher resolution than is available with other currently available devices.

Path lengths 26 and 30 are initially equal with the beam focussed at a desired initial scan depth in sample 28. As mirror 32 is moved away from lens 38, the point in the sample 28 at which the path lengths are equal is scanned to successively greater depths within the sample. At each point in the scan, reflections occur and light scattering occurs which are a function of the refractive index variation for the material through which the light is passing and of such index boundaries. Interference fringes occur for depth points in the sample where the difference between the path length to the point in the sample ($L_s$) and the path length to the current mirror location ($L_m$) differ by less than the coherence length (CL) of the light source (i.e. $L_s L_m < CL$). Therefore, the coherence length of the light source determines available system resolution. This is the reason for keeping coherence length as low as possible.

The interferometric output from coupler 22 or 70 is thus indicative of reflections or scattering obtained at a particular depth within the sample. The successive interferometric outputs obtained during a scan form an envelope signal such as that shown in FIG. 4 which normally has peaks at optical junctions within the samples where reflections are normally maximum and may have some lesser peaks in a predetermined pattern, depending on the scattering characteristics of the medium at the scan depth.

Figure 5A:
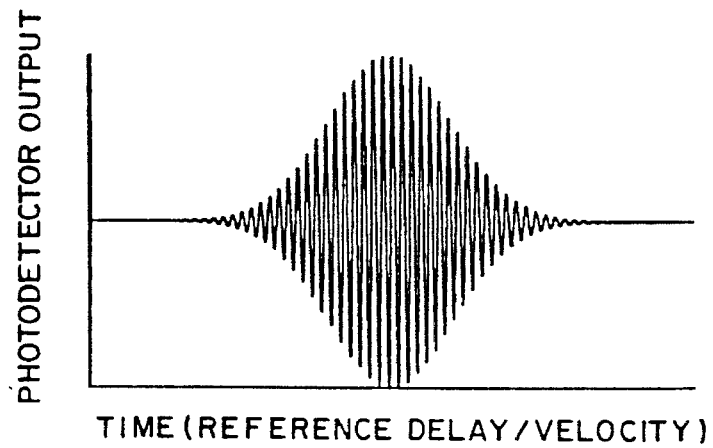
FIG. 5A is an enlarged diagram of a portion of an output waveform such as that shown in FIG. 3, illustrating the modulation frequency on which such envelope is superimposed.
Figure 5B:
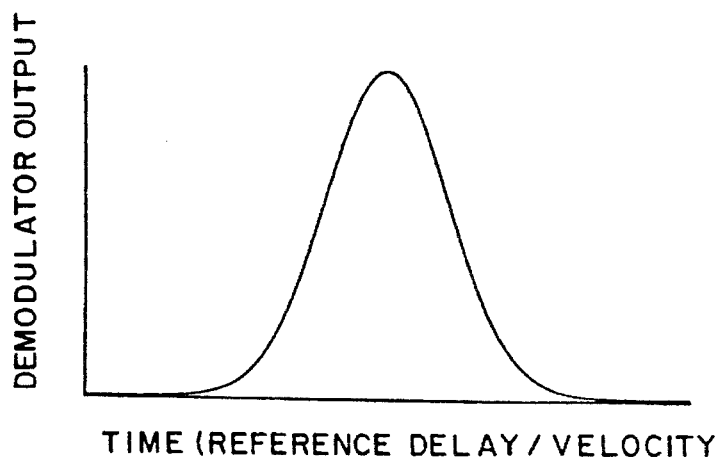
FIG. 5B is a diagram of the waveform of FIG. 5A after demodulation.

When the mirror is being scanned at a velocity V, a Doppler shift frequency having a frequency $f_D = 2V/\lambda$, where V is the velocity at which the mirror is moved and $\lambda$ is the wavelength of source 12, is superimposed on the envelope signal as shown for a small portion of an intensity output in FIG. 5A. FIG. 5B shows this same output portion after demodulation. From the equation indicated above, it is seen that the Doppler shift frequency is dependent on the wavelength of source 12. Thus, for the embodiment shown in FIG. 3, where two separate optical energy sources 12A and 12B are provided, the interferometric output from coupler 70 will contain two separate envelopes which are a function of the differences in absorption and reflection at the different wavelengths, and each interference output will be modulated at a different Doppler shift frequency. Thus, as previously indicated, the bandpass filter 78 in each demodulator 46 may be selected to have a center frequency and bandwidth for a different one of the Doppler shift frequencies, or optical filtering with multiple detectors may be utilized, to permit detection and separation of these two signals.

The ability to perform the interferometric detection at two or more different wavelengths offers unique advantages. These advantages arise from the fact that the absorption, reflection and other optical characteristics of various sample materials vary with wavelength. Thus, taking measurements at two or more wavelengths permits the spectral characterization of optical properties of the sample such as the wavelength dependent absorption and scattering thereof. In particular, the log rate of attenuation of back scatter is different for different materials and, for a given material, may vary with wavelength. By observing the back scatter pattern at different wavelengths from a substance, and possibly by observing the average rate of back scatter or reflection attenuation from layers of the sample, information concerning the material of the layer or various properties of such material may be obtained. The measurement of various spectral properties may be of interest in themselves and may also be used to distinguish between two sample layers, for example, two tissue layers that it is normally difficult to distinguish with single wavelength measurements because of their similar optical properties. In particular, by taking ratios at each of the wavelengths, spurious effects such as misalignment are compensated for permitting boundaries to be more easily and accurately identified. Basically, such boundaries are identified by looking at ratios rather than absolute values.

Figure 4:
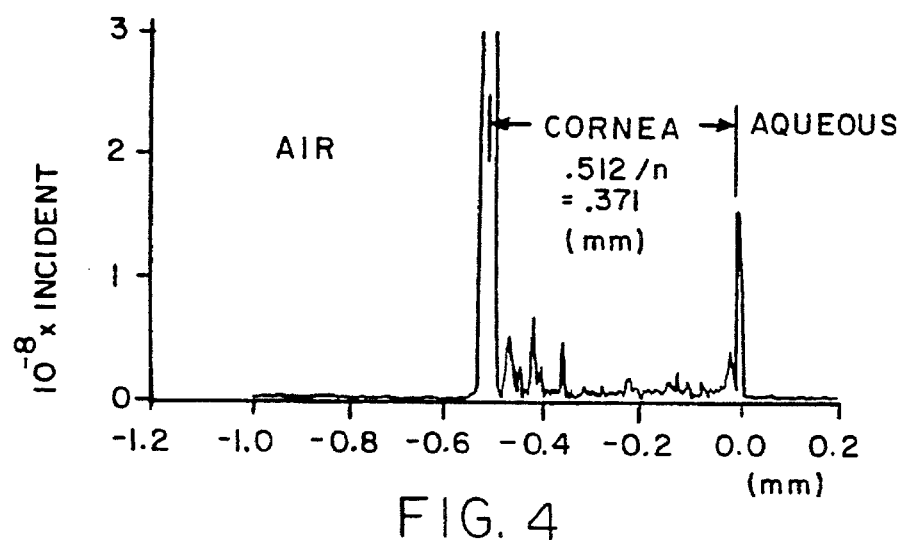
FIG. 4 is a diagram of the envelope of a scan output which might be obtained utilizing the embodiments of FIGS. 1–3.

FIG. 4 illustrates an alternative embodiment of the invention utilizing polarized light to detect birefringence. For this embodiment of the invention, light from light source 12 is polarized in a polarizer 90 sandwiched between a pair of lenses 92 before being applied to a polarization maintaining (high birefrigence) fiber 94. For purposes of illustration, polarizer 90 is shown as vertically polarizing light from source 12, vertical polarization being one of the modes of fiber 94. Fiber 94 is connected to a polarization maintaining coupler 96 which outputs the vertically polarized light on polarization maintaining fibers 98 and 100. Fiber 98 terminates in a focussing lens 102, the optical output from which is applied through a quarter wave retardation plate 104 to sample 78. Plate 104 is preferably a zero order or low order plate which is placed and oriented in a manner so that circularly polarized light is incident on sample 28. In the absence of sample birefringence, plate 104 converts reflected light passing therethrough to fiber 98 into horizontal polarization. In the presence of sample birefringence which causes light to travel at different speeds through the layer depending on polarization, the light reflected from sample layers which are in, or deeper than, the birefringent sample structures will in general return to the fiber in elliptical polarization states.

In the reference arm, the vertically polarized light in fiber 100 is focussed by lens 102 and a quarter-wavelength retardation plate 110 to mirror 32. Plate 110, which is also preferably zero order or low order, is oriented in such a manner that light applied to the mirror is elliptically polarized and reflections from the mirror which are returned to fiber 100 are in a linear polarization state with equal horizontal and vertical components. The sample and reference reflections are recombined with approximate interferometric fringes in coupler 96 and applied to a polarization maintaining fiber 112. Fiber 112 terminates in a lens 114 leading to a polarizing beam splitter 116, with horizontally polarized light from the beam splitter being applied to detector 43C and vertically polarized light from the beam splitter being applied to detector 42D. Lens 114 and polarizing beam splitter 116 may be replaced by a fiber polarizing beam splitter.

Figure 6:
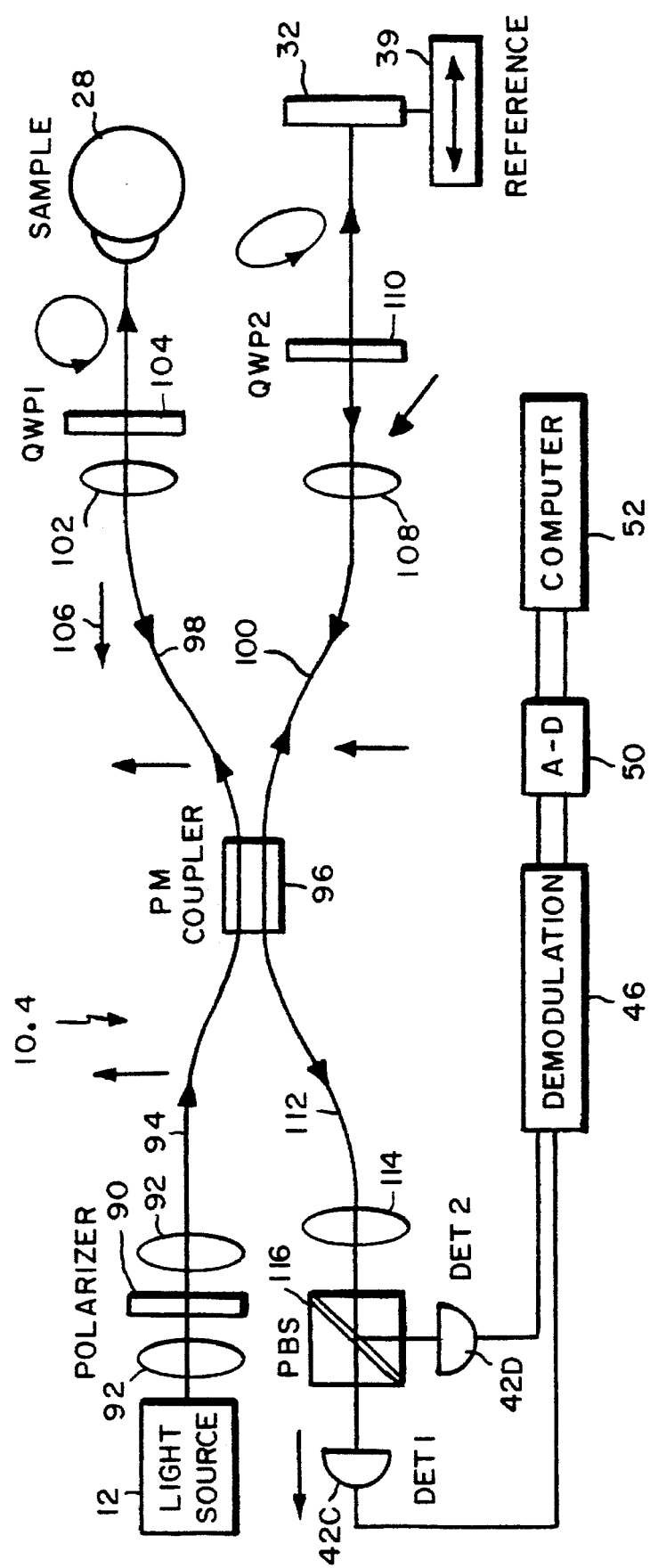
FIG. 6 is a schematic block diagram of a third fiber optic embodiment of the invention utilizing polarized light to detect birefringence.
Figure 7A:
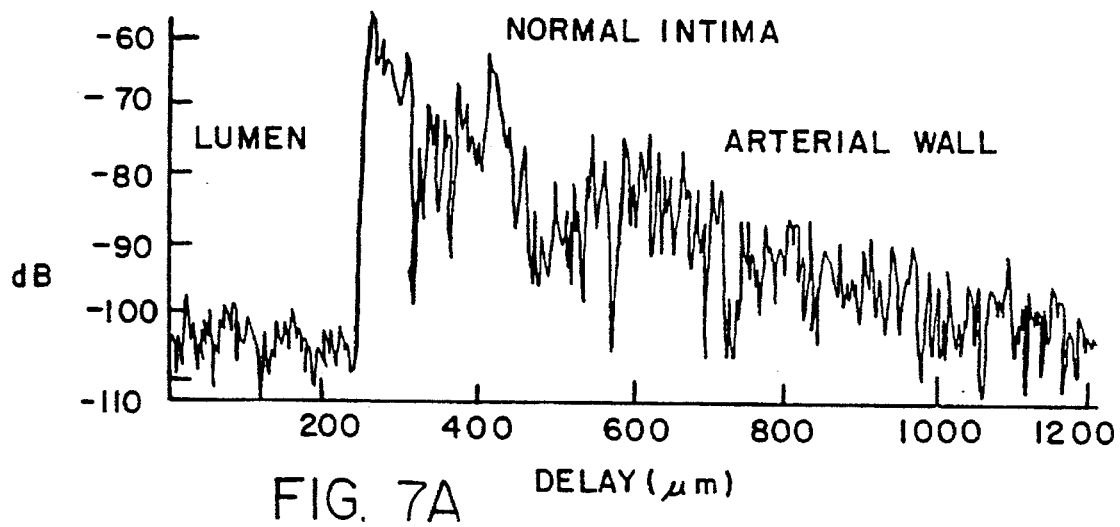
FIGS. 7A–7C are diagrams obtained using an embodiment such as that shown in FIGS. 1–3 and 6 to scan a human aorta which is normal, contains fatty plaque, and contains calcified plaque, respectively.
Figure 7B:
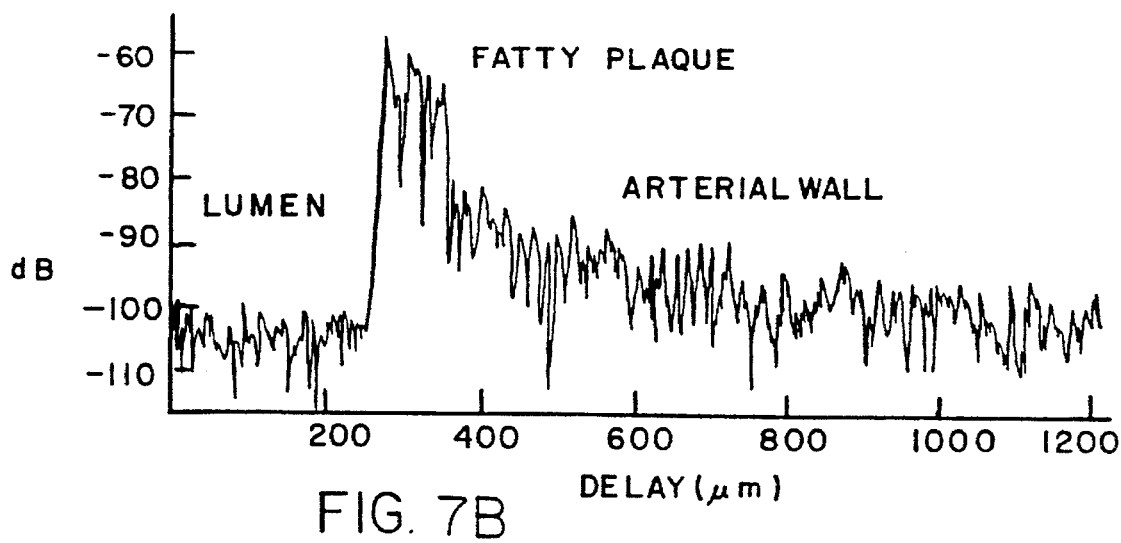
Figure 7C:
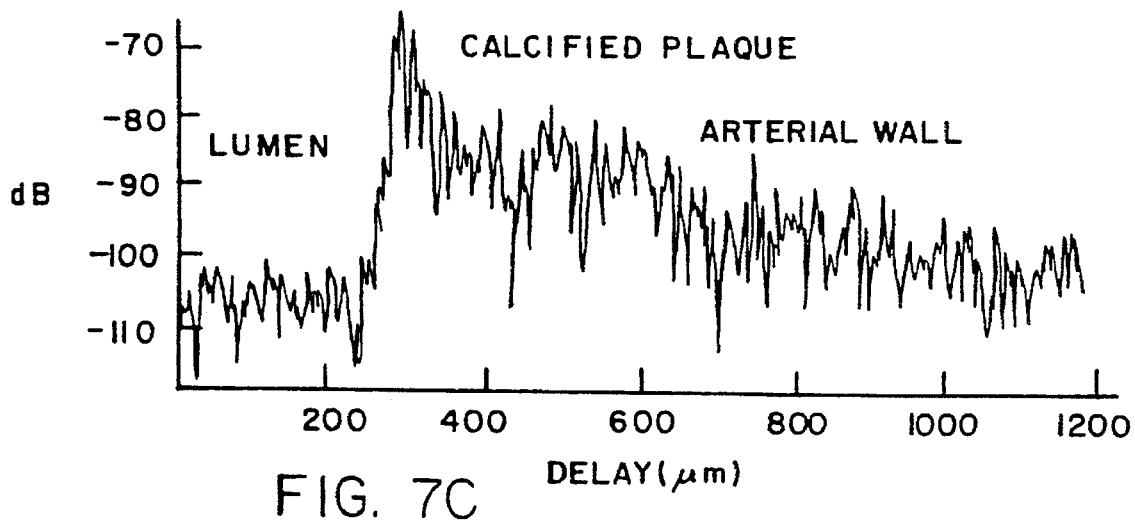

The interferometric signals detected by the two detectors, which signals are both at the same Doppler shift frequency, are separately processed in demodulators 46 and A/D converters 50 (the separate demodulators and A/D converters being shown for simplicity as single units in FIG. 6) to produce two interferometric signals, a horizontal amplitude component I1 and a vertical amplitude component I2. These signals are applied to computer 52 and can be used therein to determine the round trip birefringent retardation $\phi$ in the sample light path $$\phi = \arctan |I_2/I_1|$$

and to determine the amplitude $|I_r|$ for the sample reflection.

$$|I_r| = |I_{1r}|^2 + |I_{2r}|^2$$

Thus, by measuring the relative amplitude and phase of the two detector outputs, information on the relative phase retardation along the sample principal axes are obtained as a function of sample depth.

Birefringence is observe in structures in the eye such as the nerve fiber layer of the retina, as well as in other highly ordered biological tissues, crystals and other structures. Changes in eye nerve fiber layer thickness of 10–20 micrometers may be significant interval changes in glaucoma, and may presage the development of optic nerve head cupping and other visual field loss. Prior art techniques for measuring retinal thickness have only had a resolution on the order of 40 micrometers. However, the apparatus shown in FIG. 4 can detect the thickness of the birefringent retinal nerve fiber layer with a resolution of 10 microns. Back scattering from inside the retinal nerve fiber layer (RNFL) can be identified because the refringent retardation of back scattering from inside the RNFL increases, as for other birefringent surfaces, with depth. The range of depth over which the birefringent retardation is changing is the thickness of the RNFL and the rate of change of birefringent retardation (total retardation divided by the thickness of the RNFL) can provide a measure of the nerve axon density inside the RNFL. The back scattering and reflections from layers deeper than the RNFL will acquire a constant amount of birefringent retardation.

The ability to make such nerve fiber layer measurements provides a marked advantage in the early detection of glaucoma and in the objective assessment of progression of glaucomatous damage. Thus, weak back scattering signals from retinal substructures could be measured and could yield direct measurements of not only the overall retinal thickness, but the thickness of component sublayers as well.

Back scattered light can also be detected from the first few millimeters of turbid tissue samples such as arterial plaque and normal arterial wall. FIGS. 4A–4C are illustrations of back scattering patterns obtained from an arterial wall which is normal and which has various types of plaque deposited thereon. The log rate of attenuation for back scatter is also different for fatty plaque than for arterial wall, providing an additional way of distinguishing plaque. A fiber optic probe of the type shown in FIG. 1 or FIG. 4 could be delivered by use of an endoscope to a desired site to provide high resolution images for use in laser angioplasty and lithotripsy. This would enhance the usability of such procedures by reducing the dangers of unintentional vessel damage and rupture. This is because not only can this technique provide finer resolution than is obtainable with prior ultrasonic techniques, but also provides the ability to distinguish between arterial plaque and normal artery wall in a number of ways, including measuring birefringence and spectral properties. The internal elastic lamina of arteries are highly birefringent, which plaques are not. Plaques also have other different spectral characteristics. Such differentiation is not easily obtained with ultrasonic techniques.

While for the preferred embodiments, mechanism 39 acts on mirror 32 to effect alteration of the reference path length for scanning the sample, what is required for sampling is that there be relative charge between the sample and reference path lengths. While generally this can most easily be accomplished by moving the reference mirror, this is not a limitation on the invention and, in appropriate applications, either one or both of the sample and the reference may be moved.

In the discussion above, the beam has been projected only along a single axis. However, by using a probe beam steering mechanism in the sample arm, the probe and/or beam may after alignment be laterally scanned on a sample area of interest to provide two-dimensional or three-dimensional information or imaging. For example, with a display 54, a tomographic image of a sample can be obtained in much the same way that such images are obtained with ultrasonic scanners.

Further, while specific fiber optic and bulk optic implementations have been shown, it is apparent that this invention could also be practiced utilizing other optical implementations and that other modifications in the specific equipment shown for performing the functions might be possible, depending on application. Thus, while the invention has been particularly shown and described above with reference to preferred embodiments, the foregoing and other changes in form and detail may be made therein by one skilled in the art without departing from the spirit and scope of the invention.

What is claimed is:

1. A system for performing selected optical measurements on a sample comprising:

a short coherence length optical radiation source at a wavelength λ;

a reference optical reflector;

a first optical path leading to said reflector;

a second optical path leading to said sample;

means for applying optical radiation from said source through the first optical path to said reflector and through the second optical path to the sample;

means for altering the relative lengths of said optical paths in accordance with a predetermined velocity profile, said profile providing for continuous alteration in said relative length at an instantaneous velocity V for each point on the profile in at least the region of said profile where said measurements are to be performed;

means for combining reflections from the reflector received through the first optical path and reflections from the sample received through the second optical path, the resulting combined optical output having interference fringes at length matched points on the two paths and having an instantaneous modulating frequency including a Doppler shift frequency at a frequency $f_D=2V/\lambda$;

means for demodulating said output; and means for processing the demodulated output to obtain information concerning said selected measurements.

2. A system as claimed in claim 1 wherein there is a predominant low frequency noise for the system, wherein the velocity V is not sufficient to result in a Doppler shift frequency $f_D$ which is higher than said predominant low frequency noise, wherein said means for altering includes means for causing a vibratory change at a frequency $f_M$ in the length of at least one of said optical paths, and wherein said means for demodulating demodulates for a modulating frequency which is a selected combination of $f_D$ and $f_M$.

3. A system as claimed in claim 1 wherein there is a predominant low frequency noise for said system, wherein the velocity V is sufficiently high so that the Doppler shift frequency $f_D$ is higher than said predominant low frequency noise, and wherein said modulating frequency is $f_D$.

4. A system as claimed in claim 3 wherein the velocity V is substantially uniform over said velocity profile, at least in the portion thereof over which measurements are being taken.

5. A system as claimed in claim 4 wherein said velocity profile is substantially a sawtooth profile having a ramp portion with a substantially uniform velocity V.

6. A system as claimed in claim 4 wherein said velocity profile is a substantially triangular velocity profile having two sides, at least one side of which is at said uniform velocity V, and wherein measurements are taken during movements along at least one side of said profile.

7. A system as claimed in claim 3 wherein said means for altering alters said first path length, wherein said velocity profile provides a velocity which is not uniform with time, resulting in variations in the instantaneous $f_D$, wherein said means for demodulating includes means for adapting to the $f_D$ frequency variations, and including means for providing position information on alterations in said first path length to said means for processing.

8. A system as claimed in claim 7 wherein said demodulating means includes filter means for controlling the frequency band about said modulating frequency which is accepted by the means for demodulating, and wherein said means for adapting includes means for expanding the frequency band about said modulating frequency which is accepted by said means for demodulating.

9. A system as claimed in claim 7 wherein said means for adapting includes means for producing a signal having a frequency which varies substantially inversely with the variation in $f_D$ caused by velocity variations, and means for mixing said signal with said output to obtain an output having a substantially constant modulating frequency.

10. A system as claimed in claim 7 wherein said velocity profile is substantially a sinewave profile.

11. A system as claimed in claim 1 wherein said means for demodulating includes a logrithmic amplifier for dynamic range compression.

12. A system as claimed in claim 1 wherein said means for demodulating includes a bandpass filter centered at said modulation frequency in a pass band which is roughly two to three times the output signal bandwidth of approximately V/CL, where CL is the coherent length of the source.

13. A system as claimed in claim 1 wherein each of said optical paths include a single mode optical fiber, and means for coupling optical energy between the optical fiber and the reflector/sample at the end of the path.

14. A system as claimed in claim 13 wherein said fibers are polarization maintaining optical fibers.

15. A system as claimed in claim 1 including means for equalizing the group velocity dispersion in the two optical paths.

16. A system as claimed in claim 15 wherein said paths are formed utilizing single mode optical fibers of substantially equal length.

17. A system as claimed in claim 1 wherein measurements are to be taken for a predetermined depth extent within the sample, and wheren the numerical aperture for the means coupling the sample and the optical fiber corresponds to a depth field equal to the said depth extent.

18. A system as claimed in claim 1 wherein said means for altering includes means for reciprocating the reflector in first and second directions substantially perpendicular to said first optical path, to, respectively, lengthen and shorten the path, measurements being taken when the reflector is moved in at least one of said directions.

19. A system as claimed in claim 18 wherein said reflector may wobble slightly as it is moved, wherein said first optical path includes an optical fiber and means for optically coupling between the fiber and the reflector, and including means for maintaining the reflector in alignment in spite of movement and wobble thereof.

20. A system as claimed in claim 19 wherein said reflector includes a corner-cube, said corner-cube functioning as said means for maintaining.

21. A system as claimed in claim 1 wherein said sample is a biological sample, said measurements being indicative of optical properties of the sample along the direction of application of the optical radiation.

22. A system as claimed in claim 21 wherein the biological sample is in the eye, the measurements being of selected optical properties in the eye.

23. A system as claimed in claim 1 wherein measurements are being taken on at least one birefringent layer; and including means for polarizing the optical radiation from said source in a selected first direction, means for altering the polarization of the-radiation differently for radiation applied to said reflector and to said sample, said means for altering causing reflected radiation from the reflector to be polarized in a selected second direction and causing reflected radiation from the sample to be polarized in a direction dependent on the birefringence of said layer, the polarized reflected radiation from the reflector and sample being interferometrically combined, means for splitting and detecting the combined output as two outputs having orthogonal polarizations, means for separately processing the two outputs to obtain separate interferometric signals, and means for combining said interferometric signals to provide selected indications of birefringence.

24. A system as claimed in claim 1 wherein said optical source includes means for providing radiation at at least two different wavelengths $\lambda_1$ and $\lambda_2$, wherein said radiation at different wavelengths are absorbed and reflected differently by the sample resulting in at least a first combined optical output modulated at a frequency $f_1$, and a second combined optical output modulated at a frequency $f_2$, and wherein said means for demodulating includes separate demodulating means for each of said combined outputs.

25. A system as claimed in claim 24 wherein each of said means for demodulating includes means for filtering in a selected band centered at the appropriate modulated frequency $f_n$.

26. A system as claimed in claim 1 wherein said radiation source is selected from sources including light emitting diodes, superluminescent diodes, pulsed laser source, and incandescent light source.

27. A system as claimed in claim 1 including means for aligning the second optical path and said sample.

28. A system as claimed in claim 27 wherein said means for aligning includes means for angularly aligning, means for linearly aligning, and means for depth aligning.

29. A system as claimed in claim 1 wherein said second optical path terminates in a probe for applying a beam of said radiation to said sample, and including means for scanning said beam in transverse direction over said sample to generate an image having a plurality of dimensions.

30. A system as claimed in claim 1 wherein said optical paths are single mode fiber-optical paths, wherein said second optical path terminates in a probe, and including an endoscope in which said probe is mounted for probing internal body cavities.

31. A method for performing selected optical measurements on a sample comprising the steps of:

causing short coherence length optical radiation of a wavelength $\lambda$ to impinge on a reference reflector and on the sample through first and second optical paths, respectively;

altering the relative lengths of said paths in accordance with a predetermined velocity profile, said profile providing for continuous alteration in said relative length at an instantaneous velocity V for each point on the profile in at least the region of said profile where said measurements are to be performed;

combining reflections from the reflector received through the first optical path and reflections from the sample received through the second optical path, the resulting combined optical output having interference fringes at length matched points on the two paths and having an instantaneous modulating frequency including a Doppler shift frequency at a frequency $f_D = 2V/\lambda$;

demodulating said output; and processing the demodulated output to obtain information concerning said selected measurements.

32. A method as claimed in claim 31 wherein said sample is a biological sample, said measurements being indicative of optical properties of the sample along the direction of application of the optical radiation.

33. A system for performing selected optical measurements on a sample having at least one birefringent layer comprising:

a short coherence length optical radiation source at a wavelength $\lambda$, said radiation being polarized in a first state;

means for defining a reference optical path and a sample optical path through which radiation from said source may bidirectionally pass;

means for altering the polarization of the radiation passing through at least one of said paths in a manner such that radiation from said source in said paths have different polarization states, reflected radiation from said sample having a polarization in a state which varies as a function of the birefringence of said layer;

means for interferometrically combining reflected radiation from said optical paths;

means for providing a controlled variation in the relative path lengths for interferometrically combined radiation;

means for splitting and detecting the interferometrically combined output as two outputs having orthogonal polarization states;

means for separately processing the two outputs to obtain separate interferometric signals; and means for combining said interferometric signals to provide a selected indication of birefringence profile.

34. A system as claimed in claim 33 wherein said optical paths are formed of polarization maintaining fibers, said reference optical path terminating in a reflector, and wherein said means for providing controlled variations controls the length of the reference path.

35. A system as claimed in claim 33 wherein said two outputs are a horizontal amplitude component and a vertical amplitude component, and wherein said means for combining includes means for utilizing said amplitude components to determine at least one of birefringent retardations in the sample and the amplitude of sample reflections.

36. A system as claimed in claim 33 wherein said two outputs are combined to provide polarization insensitive measurements.

37. A system for performing selected optical measurements on a sample comprising:

means for providing short coherence length optical radiation at at least two different wavelengths $\lambda_1$ and $\lambda_2$, at least one spectral characteristic of the sample being different between wavelengths $\lambda_1$ and $\lambda_2$;

means for defining a reference optical path and a sample optical path through which said radiation at different wavelengths may bidirectionally pass;

means for interferometrically combining reflected radiation from said optical paths, said means for combining having at least a first combined optical output modulated at a frequency $f_1$ and a second combined optical output modulated at a frequency $f_2$;

means for providing a controlled variation in the relative path lengths for interferometrically combined radiation;

means for separately demodulating said first and said second combined optical outputs; and means for processing the two outputs to obtain information concerning said selected measurements.

38. A system as claimed in claim 37 wherein said reference optical path terminates in a reflector, and wherein the means for providing controlled variation controls the length of the reference path.

39. A system as claimed in claim 37 wherein said means for separately demodulating includes means for filtering each of said combined optical outputs in a selected band centered at the appropriate modulated frequency.

40. A method for optically measuring a microstructural feature of selected biological tissue comprising the steps of:

generating a short coherence length optical signal at a selected wavelength;

passing said signal through a reference optical path and through a sample optical path terminating at said biological tissue, said paths being bidirectional to also pass reflected radiation;

interferometrically combining reflected optical signals from said optical paths;

providing a controlled variation in the relative path lengths of the interferometrically combined beams;

detecting the results of said interferometrically combining step; and processing the result of the detecting step to obtain information concerning said microstructural feature.

41. A method as claimed in claim 40 wherein said biological tissue is occular tissue located in a patient's eye, said sample optical path terminating within the patient's eye, and the reflected radiation interferometrically combined including that from said occular tissue.

42. A method as claimed in claim 41 wherein said selected biological tissue is at least one of subretinal tissue, retinal tissue, and optic nerve tissue of a patient's eye, said sample optical path terminating within the patient's eye, and the reflected radiation interferometrically combined including that from said tissue of the patient's eye.

43. A method as claimed in claim 42 wherein said method is a method of measuring retinal nerve fiber layer thickness, and wherein the reflected radiation interferometrically combined includes that from said retinal nerve fiber layer.

44. A method as claimed in claim 40 wherein said biological tissue is a birefringent tissue layer;

wherein said generating step generates an optical signal which is polarized in a first state; and including the step of altering the polarization state for the radiation passing through at least one of said paths in a manner such that the signal from said generating step in said paths have different polarization states, reflected radiation from said birefringant tissue layer having a polarization in a state which varies as a function of the birefringence of such layer;

said detecting step including the step of splitting the interferometrically combined output into two outputs having orthogonal polarization states; and said processing step including the steps of separately processing the two outputs to obtain separate interferometric signals, and combining the interferometric signals to provide information concerning the structure of said tissue layer.

45. A method as claimed in claim 44 wherein said biological tissue is birefringent occular tissue of a patient's eye, said sample optical path terminating at the patient's eye and the reflected radiation interferometrically combined including that from said occular tissue.

46. A method as claimed in claim 45 wherein said method is a method of measuring retinal nerve fiber layer thickness, said retinal nerve fiber layer being a birefringent layer and wherein the reflected radiation interferometrically combined including that from said retinal nerve fiber layer.

47. A method as claimed in claim 44 wherein said method is a method of measuring retinal nerve axon density, the retinal nerve fiber layer being a birefringent layer, and wherein said processing step includes the step of determining the rate of change in birefringent retardation with nerve fiber layer thickness.

48. A method as claimed in claim 40 wherein said generating step includes the step of generating short coherence length optical radiation at at least two different wavelengths $\lambda_1$ and $\lambda_2$, at least one spectral characteristic of the biological tissue being different between the wavelengths $\lambda_1$ and $\lambda_2$;

wherein said interferometrically combining step includes the steps of providing a first combined optical output modulated at a frequency $f_1$ and a second combined optical output modulated at a frequency $f_2$;

wherein said detecting step includes the steps of separately demodulating said first and second combined optical outputs; and wherein said processing step includes the step of processing the two outputs to obtain information concerning said microstructural feature.

49. A method as claimed in claim 48 wherein the demodulating step includes the step of filtering in a selected band centered at the appropriate modulated frequency.

50. A method as claimed in claim 48 wherein said processing step includes the step of utilizing a detected difference in spectral characteristics of a sample at different wavelengths to determine at least one of a material of the sample and a property of a sample material.

51. A method as claimed in claim 48 wherein said sample is formed of at least two layers which are composed of material having different spectral characteristics at at least one of the wavelengths $\lambda_1$ and $\lambda_2$, and wherein said processing step includes the step of utilizing a detected difference in spectral characteristics for a sample at different wavelengths to determine the boundary between said layers.

* * * * *

(12) EX PARTE REEXAMINATION CERTIFICATE (6369th)
United States Patent
Swanson et al.

(10) Number: US 5,459,570 C1
(45) Certificate Issued: Aug. 19, 2008

(54) METHOD AND APPARATUS FOR PERFORMING OPTICAL MEASUREMENTS

(75) Inventors: Eric A. Swanson, Maynard, MA (US); David Huang, Cambridge, MA (US); James G. Fujimoto, Cambridge, MA (US); Carmen A. Puliafito, Weston, MA (US); Charles P. Lin, Somerville, MA (US); Joseph S. Schuman, Boston, MA (US)

(73) Assignee: Massachusetts Institute of Technology, Cambridge, MA (US)

Reexamination Request:
No. 90/006,817, Oct. 20, 2003

Reexamination Certificate for:
Patent No.: 5,459,570
Issued: Oct. 17, 1995
Appl. No.: 08/033,194
Filed: Mar. 16, 1993

Related U.S. Application Data

(63) Continuation of application No. 07/692,877, filed on Apr. 29, 1991, now abandoned.

(51) Int. Cl.
*A61B 5/00* (2006.01)
*A61B 3/10* (2006.01)
*A61B 3/12* (2006.01)
*A61B 5/103* (2006.01)
*G01B 11/00* (2006.01)
*G01B 11/24* (2006.01)
*G01B 9/02* (2006.01)
*G01J 1/00* (2006.01)
*G01N 21/47* (2006.01)
*G02B 27/44* (2006.01)
*G02B 27/42* (2006.01)
*G02B 5/18* (2006.01)
*G11B 7/00* (2006.01)
*H01S 5/14* (2006.01)
*H01S 5/00* (2006.01)

(52) U.S. Cl. ..................................................... 356/479
(58) Field of Classification Search ................ None
See application file for complete search history.

(56) References Cited

U.S. PATENT DOCUMENTS

| | | | |
|---|---|---|---|
| 4,627,731 A | 12/1986 | Waters et al. | 356/349 |
| 4,652,131 A | 3/1987 | Fercher et al. | 356/349 |
| 4,913,142 A | 4/1990 | Kittrell | 606/7 |
| 4,928,005 A | 5/1990 | Lefevre et al. | 250/227.23 |
| 5,202,745 A | 4/1993 | Sorin et al. | 356/73.1 |
| 5,491,550 A | 2/1996 | Dabbs | 356/345 |

FOREIGN PATENT DOCUMENTS

DE   25 28 209 A1   6/1975

(Continued)

OTHER PUBLICATIONS

R.C. Youngquist et al., "Optical coherence-domain reflectometry: a new optical evaluation technique," *Optics Letters*, vol. 12, No. 3, Mar. 1987, pp. 158–160.

(Continued)

*Primary Examiner*—Margaret Rubin

(57) ABSTRACT

A method and apparatus for performing various optical measurements is provided utilizing an optical coherence domain refrectometer (OCDR). A short coherence optical radiation source applies optical radiation through like optical paths to a sample and an optical reflector. The optical reflector is movable in accordance with a predetermined velocity profile to permit interferometric scanning of the sample, the resulting output having a Doppler shift frequency modulation. This output may be demodulated and detected to obtain desired measurements and other information. Additional information may be obtained by applying radiation from two or more sources at different wavelengths to the sample and reflector and by separately demodulating the resulting outputs before processing. Birefringent information may be obtained by polarizing the optical radiation used, by suitably modifying the polarization in the sample and reference paths and by dividing the output into orthogonal polarization outputs which are separately demodulated before processing.

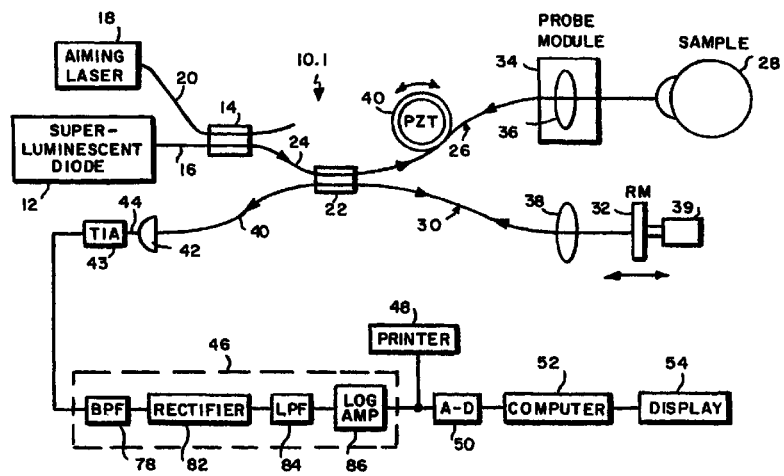

FOREIGN PATENT DOCUMENTS

| | | |
|---|---|---|
| DE | 32 01 801 A1 | 1/1982 |
| GB | 2 191 855 A | 12/1987 |
| JP | 62-155827 | 10/1987 |
| WO | WO 90/00754 | 1/1990 |
| WO | WO 92/04594 | 3/1992 |

OTHER PUBLICATIONS

K. Takada et al., "New measurement system for fault location in optical waveguide devices based on an interferometric technique," *Applied Optics*, vol. 26, No. 9, May 1, 1987, pp. 1603–1606.

B.L. Danielson et al., "Guided–wave reflectometry with micrometer resolution," *Applied Optics*, vol. 26, No. 14, Jul. 15, 1987, pp. 2836–2842.

A.F. Fercher et al., "Eye–length measurement by interferometry with partially coherent light," *Optics Letters*, vol. 13, No. 3, Mar. 1988, pp. 186–188.

P. Beaud et al., "Optical Reflectometry with Micrometer Resolution for the Investigation of Integrated Optical Devices," *IEEE Journal of Quantum Electronics*, vol. 25, No. 4, Apr. 1989, pp. 755–759.

H.H. Gilgen et al., "Submillimeter Optical Reflectometry," *Journal of Lightwave Technology*, vol. 7, No. 8, Aug. 1989, pp. 1225–1233.

M. Tateda et al., "Water Penetration Sensing Using Wavelength Tunable OTDR*," *IEEE Photonics Technology Letters*, vol. 3, No. 1, Jan. 1991, pp. 1–3.

C.K. Hitzenberger, "Optical Measurement of the Axial Eye Length by Laser Doppler Interferometry," *Investigative Ophthalmology & Visual Science*, vol. 32, No. 3, Mar. 1991, pp. 616–624.

M. Kobayashi et al., "Polarization–Independent Interferometric Optical–Time–Domain Reflectometer," *Journal of Lightwave Technology*, vol. 9, No. 5, May 1991, pp. 623–628.

M. Kobayashi et al., "Optical Fiber Component Characterization by High–Intensity and High–Spatial–Resolution Interferometric Optical–Time–Domain Reflector," *IEEE Photonics Technology Letters*, vol. 3, No. 6, Jun. 1991, pp. 564–566.

K. Takada et al., "Rayleigh backscattering measurement of single–mode fibers by low coherence optical time–domain reflectometer with 14 μm spatial resolution," *Appl. Phys. Lett.*, vol. 59, No. 2, Jul. 8, 1991, pp. 143–145.

K. Takada et al., "Resolution Control of Low–Coherence Optical Time–Domain Reflectometer Between 14 and 290 μm," *IEEE Photonics Technology Letters*, vol. 3, No. 7, Jul. 1991, pp. 676–678.

D. Huang et al., "Micron–Resolution Ranging of Cornea Anterior Chamber by Optical Reflectometry," *Lasers in Surgery and Medicine*, vol. 11 (1991), pp. 419–425.

K. Takada et al., "Phase–noise and shot–noise limited operations of low coherence optical time domain reflectometry," *Appl. Phys. Lett.*, vol. 29, No. 20, Nov. 11, 1991, pp. 2483–2485.

D. Huang et al., "Optical Coherence Tomography," *Science*, vol. 254, Nov. 22, 1991, pp. 1178–1181.

W.V. Sorin et al., "Simultaneous Thickness and Group Index Measurement Using Optical Low–Coherence Reflectometry," *IEEE Photonics Technology Letters*, vol. 4, No. 1, Jan. 1992, pp. 105–107.

E.A. Swanson et al., "High–speed optical coherence domain reflectometry," *Optics Letters*, vol. 17, No. 2, Jan. 15, 1992, pp. 151–153.

C.K. Hitzenberger et al., "Measurement of Corneal Thickness by Laser Doppler Interferometry," *Investigative Ophthalmology & Visual Science*, vol. 33, No. 1, Jan. 1992, pp. 98–103.

X. Clivaz et al., "High–resolution reflectometry in biological tissues," *Optics Letters*, vol. 17, No. 1, Jan. 1, 1992, pp. 4–6.

M. Davidson et al., "An application of interference microscopy to integrated circuit inspection and metrology," *Proceedings of SPIE—The International Society for Optical Engineering*, vol. 775, Mar. 4–6, 1987, pp. 233–241.

J.G. Fujimoto et al., "Femtosecond optical ranging in biological systems," *Optics Letters*, vol. 11, Mar. 1986, pp. 150–152.

A.S. Gerges et al., "A Short Coherence Length Interferometric Fibre Optic Sensor System," *Optical Fiber Sensors—Technical Digest Series*, vol. 2, No. 1, Jan. 27, 1988, pp. 56–58.

R.P. Novak et al., "Comparison between OTDR and OLCR with micrometer spatial resolution. New improved OLCR detection scheme and latest measurement results on IOC," *Technical Digest–Symposium on Optical Fiber Measurements*, 1990 (NIST/SP 792), pp. 35–38.

D. Stern et al., "Femtosecond Optical Ranging of Corneal Incision Depth," *Investigative Ophthalmology & Visual Science*, vol. 30, No. 1, Jan. 1989, pp. 99–104.

P.G. Suchoski et al., "Miniature Laser Vibrometer System with Multifunction Integrated Optic Circuit," *IEEE Photonics Technology Letters*, vol. 2, No. 2, Jan. 1990, pp. 81–82.

B.S. Lee et al., "Profilometry with a coherence scanning microscope," *Applied Optics*, vol. 29, No. 26, Sep. 10, 1990, pp. 3784–3788.

*Noninvasive Diagnostic Techniques in Ophthalmology*, Chapt. 28 by J.F. Bille et al., "Scanning Laser Tomography of the Living Human Eye," published by Springer–Verlag (1990), pp. 528–547.

C.K. Hitzenberger et al., "Eye length measurement by Laser Doppler Interferometry (LDI)," *Optics in Medicine, Biology and Environmental Research* (Series of the International Society on Optics Within Life Sciences—presented in Germany), vol. 1, Aug. 1–16, 1990, pp. 232–235.

H. Park et al., "High resolution optical ranging system," *Applied Optics*, vol. 20, No. 14, Jul. 15, 1981, pp. 2389–2394.

A.J. den Boef, "Two–wavelength scanning spot interferometer using single–frequency diode lasers," *Applied Optics*, vol. 27, No. 2, Jan. 15, 1988, pp. 306–311.

A.F. Fercher et al., "Measurement of Intraocular Distances by an Optical Heterodyne Technique Using Partially Coherent Light," *Holography and Speckle Phenomena and their Industrial Application—Proceedings of the International Workshop*, Dec. 12–17, 1988, Editor R.S. Sirohi, pp. cover sheet, copyright sheet, preface, 467–471.

C.K. Hitzenberger, "Optical Measurement of the Axial Eye Length by Laser Doppler Interferometry," *Investigative Ophthalmology & Visual Science*, vol. 32, No. 3, Mar. 1991, pp. 624.

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 33–51 is confirmed.

Claim 27 is cancelled.

Claims 1–2, 7, 13, 15, 17, 23–24 and 28–31 are determined to be patentable as amended.

Claims 3–6, 8–12, 14, 16, 18–22, 25–26 and 32, dependent on an amended claim, are determined to be patentable.

New claims 52–379 are added and determined to be patentable.

1. A system for performing selected optical measurements on a sample comprising:
   a short coherence length optical radiation source at a wavelength λ;
   a reference optical reflector;
   a first optical path leading to said reflector;
   a second optical path leading to said sample, *said optical path including a steering mechanism for laterally scanning a beam of said optical radiation over said sample*;
   means for applying optical radiation from said source through the first optical path to said reflector and through the second optical path to the sample;
   means for altering the relative lengths of said optical paths in accordance with a predetermined velocity profile, said profile providing for continuous alteration in said relative length at an instantaneous velocity V for each point on the profile in at least the region of said profile where said measurements are to be performed;
   means for combining reflections from the reflector received through the first optical path and reflections from the sample received through the second optical path, the resulting combined optical output having interference fringes at length matched points on the two paths and having an instantaneous modulating frequency including a Doppler shift frequency at a frequency $f_D=2V/\lambda$;
   means for demodulating said ouptut; and
   means for processing the demodulated output to obtain information concerning said selected measurements, *said information being in the form of an image having at least two dimensions.*

2. A system [as claimed in claim 1] *for performing selected optical measurements on a sample comprising:*
   *a short coherence length optical radiation source at a wavelength λ;*
   *a reference optical reflector;*
   *a first optical path leading to said reflector;*
   *a second optical path leading to said sample;*
   *means for applying optical radiation from said source through the first optical path to said reflector and through the second optical path to the sample;*
   *means for altering the relative lengths of said optical paths in accordance with a predetermined velocity profile, said profile providing for continuous alteration in said relative length at an instantaneous velocity V for each point on the profile in at least the region of said profile where said measurements are to be performed;*
   *means for combining reflections from the reflector received through the first optical path and reflections from the sample received through the second optical path, the resulting combined optical output having interference fringes at length matched points on the two paths and having an instantaneous modulating frequency including a Doppler shift frequency at a frequency $f_D=2V/\lambda$;*
   *means for demodulating said output; and*
   *means for processing the demodulated output to obtain information concerning said selected measurements* wherein there is a predominant low frequency noise for the system, wherein the velocity V is not sufficient to result in a Doppler shift frequency $f_D$ which is higher than said predominant low frequency noise, wherein said means for altering includes means for causing a vibratory change at a frequency $f_M$ in the length of at least one of said optical paths, and wherein said means for demodulating demodulates for a modulating frequency which is a selected combination of $f_D$ and $f_M$.

7. A system [as claimed in claim 3] *for performing selected optical measurements on a sample comprising:*
   *a short coherence length optical radiation source at a wavelength λ;*
   *a reference optical reflector;*
   *a first optical path leading to said reflector;*
   *a second optical path leading to said sample;*
   *means for applying optical radiation from said source through the first optical path to said reflector and through the second optical path to the sample;*
   *means for altering the relative lengths of said optical paths in accordance with a predetermined velocity profile, said profile providing for continuous alteration in said relative length at an instantaneous velocity V for each point on the profile in at least the region of said profile where said measurements are to be performed;*
   *means for combining reflections from the reflector received through the first optical path and reflections from the sample received through the second optical path, the resulting combined optical output having intereference fringes at length matched points on the two paths and having an instantaneous modulating frequency including a Doppler shift frequency at a frequency $f_D=2V/\lambda$;*
   *means for demodulating said output; and*
   *means for processing the demodulated output to obtain information concerning said selected measurements* wherein said means for altering alters said first path length, wherein said velocity profile provides a velocity which is not uniform with time, resulting in variations in the instantaneous $f_D$, wherein said means for demodulating includes means for adapting to the $f_D$ frequency variations, and including means for providing position information on alterations in said first path length to said means for processing.

13. A system [as claimed in claim 1] *for performing selected optical measurements on a sample comprising:*
   *a short coherence length optical radiation source at a wavelength λ;*
   *a reference optical reflector;*
   *a first optical path leading to said reflector;*
   *a second optical path leading to said sample;*
   *means for applying optical radiation from said source through the first optical path to said reflector and through the second optical path to the sample;*
   *means for altering the relative lengths of said optical paths in accordance with a predetermined velocity profile, said profile providing for continuous alteration in said relative length at an instantaneous velocity V for each point on the profile in at least the region of said profile where said measurements are to be performed;*
   *means for combining reflections from the reflector received through the first optical path and reflections from the sample received through the second optical path, the resulting combined optical output having interference fringes at length matched points on the two paths and having an instantaneous modulating frequency including a Doppler shift frequency at a frequency $f_D=2V/\lambda$;*
   *means for demodulating said output; and*
   *means for processing the demodulated output to obtain information concerning said selected measurements wherein each of said optical paths include a single mode optical fiber, and means for coupling optical energy between the optical fiber and the reflector/ sample at the end of the path.*

15. A system [as claimed in claim 1] *for performing selected optical measurements on a sample comprising:*
   *a short coherence length optical radiation source at a wavelength λ;*
   *a reference optical reflector;*
   *a first optical path leading to said reflector;*
   *a second optical path leading to said sample;*
   *means for applying optical radiation from said source through the first optical path to said reflector and through the second optical path to the sample;*
   *means for altering the relative lengths of said optical paths in accordance with a predetermined velocity profile, said profile providing for continuous alteration in said relative length at an instantaneous velocity V for each point on the profile in at least the region of said profile where said measurements are to be performed;*
   *means for combining reflections from the reflector received through the first optical path and reflections from the sample received through the second optical path, the resulting combined optical output having interference fringes at length matched points on the two paths and having an instantaneous modulating frequency including a Doppler shift frequency at a frequency $f_D=2V/\lambda$;*
   *means for demodulating said output; and*
   *means for processing the demodulated output to obtain information concerning said selected measurements including means for equalizing the group velocity dispersion in the two optical paths.*

17. A system [as claimed in claim 1] *for performing selected optical measurements on a sample comprising:*
   *a short coherence length optical radiation source at a wavelength λ;*
   *a reference optical reflector;*
   *a first optical path leading to said reflector;*
   *a second optical path leading to said sample wherein the second optical path includes a fiber and a means for coupling optical energy between the optical fiber and the sample;*
   *means for applying optical radiation from said source through the first optical path to said reflector and through the second optical path to the sample;*
   *means for altering the relative lengths of said optical paths in accordance with a predetermined velocity profile, said profile providing for continuous alteration in said relative length at an instantaneous velocity V for each point on the profile in at least the region of said profile where said measurements are to be performed;*
   *means for combining reflections from the reflector received through the first optical path and reflections from the sample received through the second optical path, the resulting combined optical output having interference fringes at length matched points on the two paths and having an instantaneous modulating frequency including a Doppler shift frequency at a frequency $f_D=2V/\lambda$;*
   *means for demodulating said output; and*
   *means for processing the demodulated output to obtain information concerning said selected measurements wherein measurements are to be taken for a predetermined depth extent within the sample, and wheren the numerical aperture for the means coupling the sample and the optical fiber corresponds to a depth field equal to the said depth extent.*

23. A system [as claimed in claim 1] *for performing selected optical measurements on a sample comprising:*
   *a short coherence length optical radiation source at a wavelength λ;*
   *a reference optical reflector;*
   *a first optical path leading to said reflector;*
   *a second optical path leading to said sample;*
   *means for applying optical radiation from said source through the first optical path to said reflector and through the second optical path to the sample;*
   *means for altering the relative lengths of said optical paths in accordance with a predetermined velocity profile, said profile providing for continuous alteration in said relative length at an instantaneous velocity V for each point on the profile in at least the region of said profile where said measurements are to be performed;*
   *means for combining reflections from the reflector received through the first optical path and reflections from the sample received through the second optical path, the resulting combined optical output having interference fringes at length matched points on the two paths and having an instantaneous modulating frequency including a Doppler shift frequency at a frequency $f_D=2V/\lambda$;*
   *means for demodulating said output; and*
   *means for processing the demodulated output to obtain information concerning said selected measurements, wherein measurements are being taken on at least one birefringent layer; and*
   *including means for polarizing the optical radiation from said source in a selected first direction, means for altering the polarization of the-radiation differently for radiation applied to said reflector and to said sample,* said means for altering causing reflected radiation from the reflector to be polarized in a selected second direction and causing reflected radiation from the sample to be polarized in a direction dependent on the birefringence of said layer, the polarized reflected radiation from the reflector and sample being interferometrically combined, means for splitting and detecting the combined output as two outputs having orthogonal polarizations, means for separately processing the two outputs to obtain separate interferometric signals, and means for combining said interferometric signals to provide selected indications of birefringence.

24. A system [as claimed in claim 1] *for performing selected optical measurements on a sample comprising:*
   *a short coherence length optical radiation source at a wavelength $\lambda$;*
   *a reference optical reflector;*
   *a first optical path leading to said reflector;*
   *a second optical path leading to said sample;*
   *means for applying optical radiation from said source through the first optical path to said reflector and through the second optical path to the sample;*
   *means for altering the relative lengths of said optical paths in accordance with a predetermined velocity profile, said profile providing for continuous alteration in said relative length at an instantaneous velocity V for each point on the profile in at least the region of said profile where said measurements are to be performed;*
   *means for combining reflections from the reflector received through the first optical path and reflections from the sample received through the second optical path, the resulting combined optical output having interference fringes at length matched points on the two paths and having an instantaneous modulating frequency including a Doppler shift frequency at a frequency $f_D=2V/\lambda$;*
   *means for demodulating said output; and*
   *means for processing the demodulated output to obtain information concerning said selected measurements wherein said optical source includes means for providing radiation at at least two different wavelengths $\lambda_1$ and $\lambda_2$, wherein said radiation at different wavelengths are absorbed and reflected differently by the sample resulting in at least a first combined optical output modulated at a frequency $f_1$, and a second combined optical output modulated at a frequency $f_2$, and wherein said means for demodulating includes separate demodulating means for each of said combined outputs.*

28. A system [as claimed in claim 27] *for performing selected optical measurements on a sample comprising:*
   *a short coherence length optical radiation source at a wavelength $\lambda$;*
   *a reference optical reflector;*
   *a first optical path leading to said reflector;*
   *a second optical path leading to said sample;*
   *means for applying optical radiation from said source through the first optical path to said reflector and through the second optical path to the sample;*
   *means for altering the relative lengths of said optical paths in accordance with a predetermined velocity profile, said profile providing for continuous alteration in said relative length at an instantaneous velocity V for each point on the profile in at least the region of said profile where said measurements are to be performed;*
   *means for combining reflections from the reflector received through the first optical path and reflections from the sample received through the second optical path, the resulting combined optical output having interference fringes at length matched points on the two paths and having an instantaneous modulating frequency including a Doppler shift frequency at a frequency $f_D=2V/\lambda$;*
   *means for demodulating said output;*
   *means for processing the demodulated output to obtain information concerning said selected measurements;*
   *means for aligning the second optical path and said sample; and wherein said means for aligning includes means for angularly aligning, means for linearly aligning, and means for depth aligning.*

29. A system [as claimed in claim 1] *for performing selected optical measurements on a sample comprising:*
   *a short coherence length optical radiation source at a wavelength $\lambda$;*
   *a reference optical reflector;*
   *a first optical path leading to said reflector;*
   *a second optical path leading to said sample;*
   *means for applying optical radiation from said source through the first optical path to said reflector and through the second optical path to the sample;*
   *means for altering the relative lengths of said optical paths in accordance with a predetermined velocity profile, said profile providing for continuous alteration in said relative length at an instantaneous velocity V for each point on the profile in at least the region of said profile where said measurements are to be performed;*
   *means for combining reflections from the reflector received through the first optical path and reflections from the sample received through the second optical path, the resulting combined optical output having interference fringes at length matched points on the two paths and having an instantaneous modulating frequency including a Doppler shift frequency at a frequency $f_D=2V/\lambda$;*
   *means for demodulating said output; and*
   *means for processing the demodulated output to obtain information concerning said selected measurements and wherein said second optical path terminates in a probe for applying a beam of said radiation to said sample, and including means for scanning said beam in transverse direction over said sample to generate an image having a plurality of dimensions.*

30. A system [as claimed in claim 1] *for performing selected optical measurements on a sample comprising:*
   *a short coherence length optical radiation source at a wavelength $\lambda$;*
   *a reference optical reflector;*
   *a first optical path leading to said reflector;*
   *a second optical path leading to said sample;*
   *means for applying optical radiation from said source through the first optical path to said reflector and through the second optical path to the sample;*
   *means for altering the relative lengths of said optical paths in accordance with a predetermined velocity profile, said profile providing for continuous alteration in said relative length at an instantaneous velocity V for each point on the profile in at least the region of said profile where said measurements are to be performed;*
   *means for combining reflections from the reflector received through the first optical path and reflections* from the sample received through the second optical path, the resulting combined optical output having interference fringes at length matched points on the two paths and having a instantaneous modulating frequency including a Doppler shift frequency at a frequency $f_D=2V/\lambda$;

means for demodulating said output; and means for processing the demodulated output to obtain information concerning said selected measurements and wherein said optical paths are single mode fiber-optical paths, wherein said second optical path terminates in a probe, and including an endoscope in which said probe is mounted for probing internal body cavities.

31. A method for performing selected optical measurements on a sample comprising the steps of:

causing short coherence length optical radiation of a wavelength λ to impinge on a reference reflector and on the sample through first and second optical paths, respectively;

laterally scanning the radiation in a transverse direction over the sample;

altering the relative lengths of said paths in accordance with a predetermined velocity profile, said profile providing for continuous alteration in said relative length at an instantaneous velocity V for each point on the profile in at least the reigon of said profile where said measurements are to be performed;

combining reflections from the reflector received through the first optical path and reflections from the sample received through the second optical path, the resulting combined optical output having interference fringes at length matched points on the two paths and having an instantaneous modulating frequency including a Doppler shift frequency at a frequency $f_{D=}2V/\lambda$;

demodulating said output; and processing the demodulated output to obtain information concerning said selected measurements, *said information being in the form of an image having at least two dimensions.*

52. *A system as claimed in claim 1, wherein there is a predominant low frequency noise for the system, wherein the velocity V is not sufficient to result in a Doppler shift frequency $f_D$ which is higher than said predominant low frequency noise, wherein said means for altering includes means for causing a vibratory change at a frequency $f_M$ in the length of at least one of said optical paths, and wherein said means for demodulating demodulates for a modulating frequency which is a selected combination of $f_D$ and $f_M$.*

53. *A system as claimed in claim 1, including means for equalizing the group velocity dispersion in the two optical paths.*

54. *A system as claimed in claim 53, wherein said paths are formed utilizing single mode optical fibers of substantially equal length.*

55. *A system as claimed in claim 1, wherein the second optical path includes a fiber and a means for coupling optical energy between the optical fiber and the sample at the end of the path and wherein measurements are to be taken for a predetermined depth extent within the sample, and wherein the numerical aperture for the means coupling the sample and the optical fiber corresponds to a depth field equal to the said depth extent.*

56. *A system as claimed in claim 1, wherein measurements are being taken on at least one birefrigent layer; and including means for polarizing the optical radiation from said source in a selected first direction, means for altering the polarization of the-radiation differently for radiation applied to said reflector and to said sample, said means for altering causing reflected radiation from the reflector to be polarized in a selected second direction and causing reflected radiation from the sample to be polarized in a direction dependent on the birefringence of said layer, the polarized reflected radiation from the reflector and sample being interferometrically combined, means for splitting and detecting the combined output as two outputs having orthogonal polarizations, means for separately processing the two outputs to obtain separate interferometric signals, and means for combining said interferometric signals to provide selected indications of birefringence.*

57. *A system as claimed in claim 1, wherein said optical source includes means for providing radiation at at least two different wavelengths $\lambda_1$ and $\lambda_2$, wherein said radiation at different wavelengths are absorbed and reflected differently by the sample resulting in at least a first combined optical output modulated at a frequency $f_1$, and a second combined optical output modulated at a frequency $f_2$, and wherein said means for demodulating includes separate demodulating means for each of said combined outputs.*

58. *A system as claimed in claim 57, wherein each of said means for demodulating includes means for filtering in a selected band centered at the appropriate modulated frequency $f_n$.*

59. *A system as claimed in claim 1, including means for aligning the second optical path and said sample.*

60. *A system as claimed in claim 59, wherein said means for aligning includes means for angularly aligning, means for linearly aligning, and means for depth aligning.*

61. *A system as claimed in claim 1, wherein said optical paths are single mode fiber-optical paths, wherein said second optical path terminates in a probe, and including an endoscope in which said probe is mounted for probing internal body cavities.*

62. *A system as claimed in claim 1, wherein said image is in the form of a tomographic image.*

63. *A system as claimed in claim 1, wherein said means for demodulating the output includes dynamic range compression.*

64. *The system as claimed in claim 63, wherein a logarithmic amplifier is utilized in performing the dynamic range compression.*

65. *A system as claimed in claim 1, wherein said optical path further includes an endoscope for probing internal body cavities.*

66. *A system as claimed in claim 1, further including a second light source for generating a visible beam of radiation to facilitate alignment.*

67. *A system as claimed in claim 1, wherein at least one of said optical paths includes an optical fiber.*

68. *A system as claimed in claim 67, wherein said optical fiber is a single mode optical fiber.*

69. *A system as claimed in claim 67, wherein at least one end of the optical fiber is angled polished.*

70. *A system as claimed in claim 67, wherein at least one end of the optical fiber includes an anti-reflection coating.*

71. *A system as claimed in claim 1, wherein each of said first and second optical paths includes an optical fiber.*

72. *A system as claimed in claim 71, wherein at least one end of each optical fiber is angled polished.*

73. *A system as claimed in claim 71, wherein at least one end of each optical fiber includes an anti-reflection coating.*

74. *A system as claimed in claim 71, wherein the lengths of the fibers are substantially equal.*

75. A system as claimed in claim 71, wherein said optical fibers are single mode optical fibers.

76. A system as claimed in claim 1, wherein said sample is a biological sample.

77. A system as claimed in claim 76, wherein the biological sample is the eye.

78. A system as claimed in claim 76, wherein the biological sample is the retina.

79. A system as claimed in claim 76, wherein the optical measurements are of retinal thickness.

80. A system as claimed in claim 76, wherein the optical measurements are of the thickness of component sublayers of the retina.

81. A system as claimed in claim 76, wherein the optical measurements are of the retinal nerve fiber layer.

82. A system as claimed in claim 76, wherein the biological sample is the skin.

83. A system as claimed in claim 1, wherein said image has a longitudinal resolution of approximately 10 micrometers.

84. A system as claimed in claim 1, wherein said radiation source has a coherence length of less than 10 micrometers.

85. A system as claimed in claim 1, further including a lens for focusing radiation onto the reference optical reflector.

86. A system as claimed in claim 1, wherein the velocity at which the relative length of the optical paths are altered is greater than 1 cm/sec.

87. A system as claimed in claim 1, further including an optical material located in one of the optical paths for controlling group velocity dispersion.

88. A system as claimed in claim 87, wherein said optical material is selected to equalize the group velocity dispersion in each optical path.

89. A system as claimed in claim 1, further including an optical element in one of the optical paths for modifying the polarization of the radiation.

90. A system as claimed in claim 89, wherein said optical element is retardation plate.

91. A system as claimed in claim 90, wherein the retardation plate is zero order plate.

92. A system as claimed in claim 90, wherein the retardation plate is low order plate.

93. A system as claimed in claim 1, wherein the first optical path includes at least a common portion through which radiation travels to the reflector from the source and reflected radiation travels from the reflector to the combining means.

94. A system as claimed in claim 1, wherein said means for applying optical radiation from said source through the first and second optical paths includes a first beam splitter for splitting the radiation from the source along said first and second optical paths.

95. A system as claimed in claim 94, wherein said first beam splitter also functions to combine the reflections from the sample and the reflector.

96. A system as claimed in claim 94, further including a second beam splitter separate from said first beam splitter, said second beam splitter functioning to combine the reflections from the sample and the reflector.

97. A system as claimed in claim 1, wherein the reference optical reflector is a corner cube.

98. A system as claimed in claim 1, wherein said processing means includes an analog to digital converter.

99. A system as claimed in claim 1, further including a transimpedance amplifier for generating a voltage varying signal in response to the output of the combining means and supplying that signal to the demodulating means.

100. A system as claimed in claim 1, further including a means for generating a voltage varying signal in response to the output of the combining means and supplying that signal to the demodulating means.

101. A system as claimed in claim 1, wherein said processing means detects points of interest in the demodulated output.

102. A system as claimed in claim 1, wherein means for altering includes a means for moving said reference optical reflector.

103. A system as claimed in claim 102, wherein the reference optical reflector is moved at a velocity greater than 1 cm/sec.

104. A system as claimed in claim 102, wherein said means for moving the reference optical reflector is a resonantly driven actuator.

105. A system as claimed in claim 1, further including a camera positioned to measure radiation reflected from the sample to facilitate alignment.

106. A system as claimed in claim 1, wherein each of said first and second optical paths includes an optical fiber and wherein the velocity at which the relative length of the optical paths is altered is greater than 1 cm/sec and wherein said processing means includes an analog to digital converter.

107. A system as claimed in claim 106, wherein said means for applying optical radiation from said source through the first and second optical paths includes a beam splitter for splitting the radiation from the source along said first and second optical paths and wherein said beam splitter also functions to combine the reflections from the sample and the reflector.

108. A system as claimed in claim 107, further including an optical element in one of the optical paths for modifying the polarization of the radiation.

109. A system as claimed in claim 107 further including a means for generating a voltage varying signal in response to the output of the combining means and supplying that signal to the demodulating means.

110. A method as claimed in claim 31, wherein said image is in the form of a tomographic image.

111. A method as claimed in claim 31, wherein the step of demodulating the detected output includes performing dynamic range compression.

112. The method as claimed in claim 111, wherein a logarithmic amplifier is utilized in performing the dynamic range compression.

113. A method as claimed in claim 31, the sample is an internal body cavity which is scanned using an endoscope.

114. A method as claimed in claim 31, further including the step of generating a visible beam of radiation to facilitate alignment.

115. A method as claimed in claim 31, wherein each of said first and second optical paths includes an optical fiber.

116. A method as claimed in claim 115, wherein at least one end of each optical fiber is angled polished.

117. A method as claimed in claim 115, wherein at least one end of each optical fiber includes an anti-reflection coating.

118. A method as claimed in claim 115, wherein the lengths of the fibers are substantially equal.

119. A method as claimed in claim 115, wherein said optical fibers are single mode optical fibers.

120. A method as claimed in claim 31, wherein said sample is a biological sample.

121. A method as claimed in claim 120, wherein the biological sample is the eye.

122. A method as claimed in claim 120, wherein the biological sample is the retina.

123. A method as claimed in claim 120, wherein the optical measurements are of retinal thickness.

124. A method as claimed in claim 120, wherein the optical measurements are of the thickness of component sublayers of the retina.

125. A system as claimed in claim 120, wherein the optical measurements are of the retinal nerve fiber layer.

126. A method as claimed in claim 120, wherein the biological sample is the skin.

127. A method as claimed in claim 31, wherein said image has a longitudinal resolution of approximately 10 micrometers.

128. A method as claimed in claim 31, wherein the optical radiation has a coherence length of less than 10 micrometers.

129. A method as claimed in claim 31, further including the step of focusing radiation onto the reference reflector.

130. A method as claimed in claim 31, wherein the velocity at which the relative length of the optical paths are altered is greater than 1 cm/sec.

131. A method as claimed in claim 31, further including the step of modifying the polarization of the radiation in one of the optical paths.

132. A method as claimed in claim 131, wherein the polarization is modified using a retardation plate.

133. A method as claimed in claim 31, wherein a beam splitter is used to divide the radiation along the first and second optical paths and the same beam splitter is used to combine the reflections from the reflector and the sample.

134. A method as claimed in claim 31, wherein the processing step includes converting the detected output from an analog signal to a digital signal.

135. A method as claimed in claim 31, wherein each of said first and second optical paths includes an optical fiber and wherein the velocity at which the relative length of the optical paths is altered is greater than 1 cm/sec and wherein the processing step includes converting the detected output from an analog signal to a digital signal.

136. A method as claimed in claim 135, wherein a beam splitter is used to divide the radiation along the first and second optical paths and the same beam splitter is used to combine the reflections from the reflector and the sample.

137. A method as claimed in claim 136, further including the step of modifying the polarization of the radiation in one of the optical paths.

138. A method as claimed in claim 40, further including laterally scanning the optical signal in a transverse direction over the biological tissue and wherein said information concerning a microstructural feature is in the form of an image having at least two dimensions.

139. A method as claimed in claim 138, wherein said image is in the form of a tomographic image.

140. A method as claimed in claim 40, wherein the step of processing the result of the detecting step includes performing dynamic range compression.

141. The method as claimed in claim 140, wherein a logarithmic amplifier is utilized in performing the dynamic range compression.

142. A method as claimed in claim 40, the biological tissue is located in an internal body cavity which is accessed using an endoscope.

143. A method as claimed in claim 142, wherein said internal body cavity is a blood vessel.

144. A method as claimed in claim 143, wherein the microstructural feature includes plaque.

145. A method as claimed in claim 142, wherein said internal body cavity is an airway.

146. A method as claimed in claim 142, wherein said internal body cavity is in the digestive tract.

147. A method as claimed in claim 40, further including the step of generating a separate visible beam of radiation and using that visible beam to facilitate the second optical path.

148. A method as claimed in claim 40, wherein each of said first and second optical paths includes an optical fiber.

149. A method as claimed in claim 148, wherein at least one end of each optical fiber is angled polished.

150. A method as claimed in claim 148, wherein at least one end of each optical fiber includes an anti-reflection coating.

151. A method as claimed in claim 148, wherein the lengths of the fibers are substantially equal.

152. A method as claimed in claim 148, wherein said optical fibers are single mode optical fibers.

153. A method as claimed in claim 40, wherein the biological sample is the eye.

154. A method as claimed in claim 153, wherein the biological sample is the retina.

155. A method as claimed in claim 153, wherein the optical measurements are of retinal thickness.

156. A method as claimed in claim 153, wherein the optical measurements are of the thickness of component sublayers of the retina.

157. A method as claimed in claim 153, wherein the optical measurements are of the retinal nerve fiber layer.

158. A method as claimed in claim 40, wherein the biological sample is the skin.

159. A method as claimed in claim 138, wherein said image has a longitudinal resolution of approximately 10 micrometers.

160. A method as claimed in claim 40, wherein said optical signal has a coherence length of less than 10 micrometers.

161. A method as claimed in claim 40, wherein the velocity at which the relative path lengths of the interferometrically combined beams are altered is greater than 1 cm/sec.

162. A method as claimed in claim 40, further including the step of modifying the polarization of the radiation in one of the optical paths.

163. A method as claimed in claim 162, wherein the polarization is modified using a retardation plate.

164. A method as claimed in claim 40, wherein a beam splitter is used to divide the radiation along the first and second optical paths and the same beam splitter is used to combine the reflected optical signals from said optical paths.

165. A method as claimed in claim 40, wherein said processing step includes converting the result of the detecting step from an analog signal to a digital signal.

166. A method as claimed in claim 40, wherein each of said first and second optical paths includes an optical fiber and wherein the velocity at which the relative path lengths of the interferometrically combined beams are altered is greater than 1 cm/sec and wherein a beam splitter is used to divide the radiation along the first and second optical paths and the same beam splitter is used to combine the reflected optical signals from said optical paths.

167. A method as claimed in claim 166, further including the step of modifying the polarization of the radiation in one of the optical paths.

168. A system for performing selected optical measurements on a sample comprising:

a short coherence length optical radiation source at a wavelength $\lambda$;

a reference optical reflector;

a first optical path leading to said reflector;

a second optical path leading to said sample, said optical path including a means for scanning a beam of said optical radiation in a transverse direction over said sample;

means for applying optical radiation from said source through the first optical path to said reflector and through the second optical path to the sample;

means for altering the relative lengths of said optical paths in accordance with a predetermined velocity profile, said profile providing for continuous alteration in said relative length at an instantaneous velocity V for each point on the profile in at least the region of said profile where said measurements are to be performed;

means for combining reflections from the reflector received through the first optical path and reflections from the sample received through the second optical path, the resulting combined optical output having interference fringes at length matched points on the two paths and having an instantaneous modulating frequency including a Doppler shift frequency at a frequency $f_D=2V/\lambda$;

means for demodulating said output; and means for processing the demodulated output to obtain information concerning said selected measurements, said information being in the form of an image having at least two dimensions.

169. A system for performing selected optical measurements on a sample comprising:

a short coherence length optical radiation source at a wavelength $\lambda$;

a reference optical reflector;

a first optical path leading to said reflector;

a second optical path leading to said sample, said optical path including an endoscope for probing internal body cavities;

means for applying optical radiation from said source through the first optical path to said reflector and through the second optical path to the sample;

means for altering the relative lengths of said optical paths in accordance with a predetermined velocity profile, said profile providing for continuous alteration in said relative length at an instantaneous velocity V for each point on the profile in at least the region of said profile where said measurements are to be performed;

means for combining reflections from the reflector received through the first optical path and reflections from the sample received through the second optical path, the resulting combined optical output having interference fringes at length matched points on the two paths and having an instantaneous modulating frequency including a Doppler shift frequency at a frequency $f_D=2V/\lambda$;

means for demodulating said output; and means for processing the demodulated output to obtain information concerning said selected measurements.

170. A method for performing selected optical measurements on a sample comprising the steps of:

causing short coherence length optical radiation of a wavelength $\lambda$ to impinge on a reference reflector and on the sample through first and second optical paths, respectively, wherein the sample is an internal body cavity which is accessed using an endoscope;

altering the relative lengths of said paths in accordance with a predetermined velocity profile, said profile providing for continuous alteration in said relative length at an instantaneous velocity V for each point on the profile in at least the region of said profile where said measurements are to be performed;

combining reflections from the reflector received through the first optical path and reflections from the sample received through the second optical path, the resulting combined optical output having interference fringes at length matched points on the two paths and having an instantaneous modulating frequency including a Doppler shift frequency at a frequency $f_D=2V/\lambda$;

demodulating said output; and processing the demodulated output to obtain information concerning said selected measurements.

171. A system as claimed in claim 2, wherein said optical path includes a steering mechanism for laterally scanning a beam of said optical radiation over said sample and wherein the means for processing generates information in the form of an image having at least two dimensions.

172. A system as claimed in claim 2, including means for aligning the second optical path and said sample.

173. A system as claimed in claim 171, wherein said image is in the form of a tomographic image.

174. A system as claimed in claim 2, wherein said means for demodulating the output includes dynamic range compression.

175. The system as claimed in claim 174, wherein a logarithmic amplifier is utilized in performing the dynamic range compression.

176. A system as claimed in claim 2, wherein said optical path further includes an endoscope for probing internal body cavities.

177. A system as claimed in claim 2, further including a second light source for generating a visible beam of radiation to facilitate alignment.

178. A system as claimed in claim 2, wherein at least one of said optical paths includes an optical fiber.

179. A sytem as claimed in claim 178, wherein said optical fiber is a single mode optical fiber.

180. A system as claimed in claim 178, wherein said at least one end of the optical fiber is angled polished.

181. A system as claimed in claim 178, wherein at least one end of the optical fiber includes an anti-reflection coating.

182. A system as claimed in claim 2, wherein each of said first and second optical paths includes an optical fiber.

183. A system as claimed in claim 182, wherein at least one end of each optical fiber is angled polished.

184. A system as claimed in claim 182, wherein at least one end of each optical fiber includes an anti-reflection coating.

185. A system as claimed in claim 182, wherein the lengths of the fibers are substantially equal.

186. A system as claimed in claim 182, wherein said optical fibers are single mode optical fibers.

187. A system as claimed in claim 2, wherein said sample is a biological sample.

188. A system as claimed in claim 187, wherein the biological sample is the eye.

189. A system as claimed in claim 187, wherein the biological sample is the retina.

190. A system as claimed in claim 187, wherein the optical measurements are of retinal thickness.

191. A system as claimed in claim 187, wherein the optical measurements are of the thickness of component sublayers of the retina.

192. A system as claimed in claim 187, wherein the optical measurements are of the retinal nerve fiber layer.

193. A system as claimed in claim 187, wherein the biological sample is the skin.

194. A system as claimed in claim 171, wherein said image has a longitudinal resolution of approximately 10 micrometers.

195. A system as claimed in claim 2, wherein said radiation source has a coherence length of less than 10 micrometers.

196. A system as claimed in claim 2, further including a lens for focusing radiation onto the reference optical reflector.

197. A system as claimed in claim 2, wherein the velocity at which the relative length of the optical paths are altered is greater than 1 cm/sec.

198. A system as claimed in claim 2, further including an optical material located in one of the optical paths for controlling group velocity dispersion.

199. A system as claimed in claim 198, wherein said optical material is selected to equalize the group velocity dispersion in each optical path.

200. A system as claimed in claim 2, further including an optical element in one of the optical paths for modifying the polarization of the radiation.

201. A system as claimed in claim 200, wherein said optical element is retardation plate.

202. A system as claimed in claim 201, wherein the retardation plate is zero order plate.

203. A system as claimed in claim 202, wherein the retardation plate is low order plate.

204. A system as claimed in claim 2, wherein the first optical path includes at least a common portion through which radiation travels to the reflector from the source and reflected radiation travels from the reflector to the combining means.

205. A system as claimed in claim 2, wherein said means for applying optical radiation from said source through the first and second optical paths includes a first beam splitter for splitting the radiation from the source along said first and second optical paths.

206. A system as claimed in claim 205, wherein said first beam splitter also functions to combine the reflections from the sample and the reflector.

207. A system as claimed in claim 205, further including a second beam splitter separate from said first beam splitter, said second beam splitter functioning to combine the reflections from the sample and the reflector.

208. A system as claimed in claim 2, wherein the reference optical reflector is a corner cube.

209. A system as claimed in claim 2, wherein said processing means includes an analog to digital converter.

210. A system as claimed in claim 2, further including a transimpedance amplifier for generating a voltage varying signal in response to the output of the combining means and supplying that signal to the demodulating means.

211. A system as claimed in claim 2, further including a means for generating a voltage varying signal in response to the output of the combining means and supplying that signal to the demodulating means.

212. A system as claimed in claim 2, wherein said processing means detects points of interest in the demodulated output.

213. A system as claimed in claim 2, wherein means for altering includes a means for moving said reference optical reflector.

214. A system as claimed in claim 213, wherein the reference optical reflector is moved at a velocity greater than 1 cm/sec.

215. A system as claimed in claim 213, wherein said means for moving the reference optical reflector is a resonantly driven actuator.

216. A system as claimed in claim 2, further including a camera positioned to measure radiation reflected from the sample to facilitate alignment.

217. A system as claimed in claim 2, wherein each of said first and second optical paths includes an optical fiber and wherein the velocity at which the relative length of the optical paths is altered is greater than 1 cm/sec and wherein said processing means includes an analog to digital converter.

218. A system as claimed in claim 217, wherein said means for applying optical radiation from said source through the first and second optical paths includes a beam splitter for splitting the radiation from the source along said first and second optical paths and wherein said beam splitter also functions to combine the reflections from the sample and the reflector.

219. A system as claimed in claim 218, further including an optical element in one of the optical paths for modifying the polarization of the radiation.

220. A system as claimed in claim 218, further including a means for generating a voltage varying signal in response to the output of the combining means and supplying that signal to the demodulating means.

221. A system as claimed in claim 13, wherein said optical path includes a steering mechanism for laterally scanning a beam of said optical radiation over said sample and wherein the means for processing generates information in the form of an image having at least two dimensions.

222. A system as claimed in claim 13, wherein there is a predominant low frequency noise for the system, wherein the velocity $V$ is not sufficient to result in a Doppler shift frequency $f_D$ which is higher than said predominant low frequency noise, wherein said means for altering includes means for causing a vibratory change at a frequency $f_M$ in the length of at least one of said optical paths, and wherein said means for demodulating demodulates for a modulating frequency which is a selected combination of $f_D$ and $f_M$.

223. A system as claimed in claim 13, including means for aligning the second optical path and said sample.

224. A system as claimed in claim 221, wherein said image is in the form of a tomographic image.

225. A system as claimed in claim 13, wherein said means for demodulating the output includes dynamic range compression.

226. The system as claimed in claim 225, wherein a logarithmic amplifier is utilized in performing the dynamic range compression.

227. A system as claimed in claim 13, wherein said optical path further includes an endoscope for probing internal body cavities.

228. A system as claimed in claim 13, further including a second light source for generating a visible beam of radiation to facilitate alignment.

229. A system as claimed in claim 228, wherein at least one end of each optical fiber is angled polished.

230. A system as claimed in claim 228, wherein at least one end of each optical fiber includes an anti-reflection coating.

231. A system as claimed in claim 13, wherein the lengths of the fibers are substantially equal.

232. A system as claimed in claim 13, wherein said sample is a biological sample.

233. A system as claimed in claim 232, wherein the biological sample is the eye.

234. A system as claimed in claim 232, wherein the biological sample is the retina.

235. A system as claimed in claim 232, wherein the optical measurements are of retinal thickness.

236. A system as claimed in claim 232, wherein the optical measurements are of the thickness of component sublayers of the retina.

237. A system as claimed in claim 232, wherein the optical measurements are of the retinal nerve fiber layer.

238. A system as claimed in claim 232, wherein the biological sample is the skin.

239. A system as claimed in claim 221, wherein said image has a longitudinal resolution of approximately 10 micrometers.

240. A system as claimed in claim 13, wherein said radiation source has a coherence length of less than 10 micrometers.

241. A system as claimed in claim 13, further including a lens for focusing radiation onto the reference optical reflector.

242. A system as claimed in claim 13, wherein the velocity at which the relative length of the optical paths are altered is greater than 1 cm/sec.

243. A system as claimed in claim 13, further including an optical material located in one of the optical paths for controlling group velocity dispersion.

244. A system as claimed in claim 243, wherein said optical material is selected to equalize the group velocity dispersion in each optical path.

245. A system as claimed in claim 13, further including an optical element in one of the optical paths for modifying the polarization of the radiation.

246. A system as claimed in claim 245, wherein said optical element is retardation plate.

247. A system as claimed in claim 246, wherein the retardation plate is zero order plate.

248. A system as claimed in claim 246, wherein the retardation plate is low order plate.

249. A system as claimed in claim 13, wherein the first optical path includes at least a common portion through which radiation travels to the reflector from the source and reflected radiation travels from the reflector to the combining means.

250. A system as claimed in claim 13, wherein said means for applying optical radiation from said source through the first and second optical paths includes a first beam splitter for splitting the radiation from the source along said first and second optical paths.

251. A system as claimed in claim 250, wherein said first beam splitter also functions to combine the reflections from the sample and the reflector.

252. A system as claimed in claim 250, further including a second beam splitter separate from said first beam splitter, said second beam splitter functioning to combine the reflections from the sample and the reflector.

253. A system as claimed in claim 13, wherein the reference optical reflector is a corner cube.

254. A system as claimed in claim 13, wherein said processing means includes an analog to digital converter.

255. A system as claimed in claim 13, further including a transimpedance amplifier for generating a voltage varying signal in response to the output of the combining means and supplying that signal to the demodulating means.

256. A system as claimed in claim 13, further including a means for generating a voltage varying signal in response to the output of the combining means and supplying that signal to the demodulating means.

257. A system as claimed in claim 13, wherein said processing means detects points of interest in the demodulated output.

258. A system as claimed in claim 13, wherein means for altering includes a means for moving said reference optical reflector.

259. A system as claimed in claim 258, wherein the reference optical reflector is moved at a velocity greater than 1 cm/sec.

260. A system as claimed in claim 258, wherein said means for moving the reference optical reflector is a resonantly driven actuator.

261. A system as claimed in claim 13, further including a camera positioned to measure radiation reflected from the sample to facilitate alignment.

262. A system as claimed in claim 13, wherein the velocity at which the relative length of the optical paths is altered is greater than 1 cm/sec and wherein said processing means includes an analog to digital converter.

263. A system as claimed in claim 262, wherein said means for applying optical radiation from said source through the first and second optical paths includes a beam splitter for splitting the radiation from the source along said first and second optical paths and wherein said beam splitter also functions to combine the reflections from the sample and the reflector.

264. A system as claimed in claim 263, further including an optical element in one of the optical paths for modifying the polarization of the radiation.

265. A system as claimed in claim 263, further including a means for generating a voltage varying signal in response to the output of the combining means and supplying that signal to the demodulating means.

266. A system as claimed in claim 29, wherein there is a predominant low frequency noise for the system, wherein the velocity V is not sufficient to result in a Doppler shift frequency $f_D$ which is higher than said predominant low frequency noise, wherein said means for altering includes means for causing a vibratory change at a frequency $f_M$ in the length of at least one of said optical paths, and wherein said means for demodulating demodulates for a modulating frequency which is a selected combination of $f_D$ and $f_M$.

267. A system as claimed in claim 29, including means for aligning the second optical path and said sample.

268. A system as claimed in claim 29, wherein said image is in the form of a tomographic image.

269. A system as claimed in claim 29, wherein said means for demodulating the output includes dynamic range compression.

270. The system as claimed in claim 269, wherein a logarithmic amplifier is utilized in performing the dynamic range compression.

271. A system as claimed in claim 29, wherein said optical path further includes an endoscope for probing internal body cavities.

272. A system as claimed in claim 29, further including a second light source for generating a visible beam of radiation to facilitate alignment.

273. A system as claimed in claim 29, wherein at least one of said optical paths includes an optical fiber.

274. A system as claimed in claim 273, wherein said optical fiber is a single mode optical fiber.

275. A system as claimed in claim 273, wherein at least one end of the optical fiber is angled polished.

276. A system as claimed in claim 273, wherein at least one end of the optical fiber includes an anti-reflection coating.

277. A system as claimed in claim 29, wherein each of said first and second optical paths includes an optical fiber.

278. A system as claimed in claim 277, wherein at least one end of each optical fiber is angled polished.

279. A system as claimed in claim 277, wherein at least one end of each optical fiber includes an anti-reflection coating.

280. A system as claimed in claim 277, wherein the lengths of the fibers are substantially equal.

281. A system as claimed in claim 277, wherein said optical fibers are single mode optical fibers.

282. A system as claimed in claim 29, wherein said sample is a biological sample.

283. A system as claimed in claim 282, wherein the biological sample is the eye.

284. A system as claimed in claim 282, wherein the biological sample is the retina.

285. A system as claimed in claim 282, wherein the optical measurements are of retinal thickness.

286. A system as claimed in claim 282, wherein the optical measurements are of the thickness of component sublayers of the retina.

287. A system as claimed in claim 282, wherein the optical measurements are of the retinal nerve fiber layer.

288. A system as claimed in claim 282, wherein the biological sample is the skin.

289. A system as claimed in claim 29, wherein said image has a longitudinal resolution of approximately 10 micrometers.

290. A system as claimed in claim 29, wherein said radiation source has a coherence length of less than 10 micrometers.

291. A system as claimed in claim 29, further including a lens for focusing radiation onto the reference optical reflector.

292. A system as claimed in claim 29, wherein the velocity at which the relative length of the optical paths are altered is greater than 1 cm/sec.

293. A system as claimed in claim 29, further including an optical material located in one of the optical paths for controlling group velocity dispersion.

294. A system as claimed in claim 293, wherein said optical material is selected to equalize the group velocity dispersion in each optical path.

295. A system as claimed in claim 29, further including an optical element in one of the optical paths for modifying the polarization of the radiation.

296. A system as claimed in claim 295, wherein said optical element is retardation plate.

297. A system as claimed in claim 296, wherein the retardation plate is zero order plate.

298. A system as claimed in claim 297, wherein the retardation plate is low order plate.

299. A system as claimed in claim 29, wherein the first optical path includes at least a common portion through which radiation travels to the reflector from the source and reflected radiation travels from the reflector to the combining means.

300. A system as claimed in claim 29, wherein said means for applying optical radiation from said source through the first and second optical paths includes a first beam splitter for splitting the radiation from the source along said first and second optical paths.

301. A system as claimed in claim 300, wherein said first beam splitter also functions to combine the reflections from the sample and the reflector.

302. A system as claimed in claim 300, further including a second beam splitter separate from said first beam splitter, said second beam splitter functioning to combine the reflections from the sample and the reflector.

303. A system as claimed in claim 29, wherein the reference optical reflector is a corner cube.

304. A system as claimed in claim 29, wherein said processing means includes an analog to digital converter.

305. A system as claimed in claim 29, further including a transimpedance amplifier for generating a voltage varying signal in response to the output of the combining means and supplying that signal to the demodulating means.

306. A system as claimed in claim 29, further including a means for generating a voltage varying signal in response to the output of the combining means and supplying that signal to the demodulating means.

307. A system as claimed in claim 29, wherein said processing means detects points of interest in the demodulated output.

308. A system as claimed in claim 29, wherein means for altering includes a means for moving said reference optical reflector.

309. A system as claimed in claim 308, wherein the reference optical reflector is moved at a velocity greater than 1 cm/sec.

310. A system as claimed in claim 308, wherein said means for moving the reference optical reflector is a resonantly driven actuator.

311. A system as claimed in claim 29, further including a camera positioned to measure radiation reflected from the sample to facilitate alignment.

312. A system as claimed in claim 29, wherein each of said first and second optical paths includes an optical fiber and wherein the velocity at which the relative length of the optical paths is altered is greater than 1 cm/sec and wherein said processing means includes an analog to digital converter.

313. A system as claimed in claim 312, wherein said means for applying optical radiation from said source through the first and second optical paths includes a beam splitter for splitting the radiation from the source along said first and second optical paths and wherein said beam splitter also functions to combine the reflections from the sample and the reflector.

314. A system as claimed in claim 313, further including an optical element in one of the optical paths for modifying the polarization of the radiation.

315. A system as claimed in claim 313, further including a means for generating a voltage varying signal in response to the output of the combining means and supplying that signal to the demodulating means.

316. A system as claimed in claim 169, wherein said optical path includes a steering mechanism for laterally scanning a beam of said optical radiation over said sample and wherein the means for processing generates information in the form of an image having at least two dimensions.

317. A system as claimed in claim 169, including means for aligning the second optical path and said sample.

318. A system as claimed in claim 169, wherein there is a predominant low frequency noise for the system, wherein the velocity V is not sufficient to result in a Doppler shift frequency $f_D$ which is higher than said predominant low frequency noise, wherein said means for altering includes means for causing a vibratory change at a frequency $f_M$ in the length of at least one of said optical paths, and wherein said means for demodulating demodulates for a modulating frequency which is a selected combination of $f_D$ and $f_M$.

319. A system as claimed in claim 316, wherein said image is in the form of a tomographic image.

320. A system as claimed in claim 169, wherein said means for demodulating the output includes dynamic range compression.

321. The system as claimed in claim 320, wherein a logarithmic amplifier is utilized in performing the dynamic range compression.

322. A system as claimed in claim 169, further including a second light source for generating a visible beam of radiation to faciltiate alignment.

323. A system as claimed in claim 169, wherein at least one of said optical paths includes an optical fiber.

324. A system as claimed in claim 323, wherein said optical fiber is a single mode optical fiber.

325. A system as claimed in claim 323, wherein at least one end of the optical fiber is angled polished.

326. A system as claimed in claim 323, wherein at least one end of the optical fiber includes an anti-reflection coating.

327. A system as claimed in claim 169, wherein each of said first and second optical paths includes an optical fiber.

328. A system as claimed in claim 327, wherein at least one end of each optical fiber is angled polished.

329. A system as claimed in claim 327, wherein at least one end of each optical fiber includes an anti-reflection coating.

330. A system as claimed in claim 327, wherein the lengths of the fibers are substantially equal.

331. A system as claimed in claim 327, wherein said optical fibers are single mode optical fibers.

332. A system as claimed in claim 316, wherein said image has a longitudinal resolution of approximately 10 micrometers.

333. A system as claimed in claim 169, wherein said radiation source has a coherence length of less than 10 micrometers.

334. A system as claimed in claim 169, further including a lens for focusing radiation onto the reference optical reflector.

335. A system as claimed in claim 169, wherein the velocity at which the relative length of the optical paths are altered is greater than 1 cm/sec.

336. A system as claimed in claim 169, further including an optical material located in one of the optical paths for controlling group velocity dispersion.

337. A system as claimed in claim 336, wherein said optical material is selected to equalize the group velocity dispersion in each optical path.

338. A system as claimed in claim 169, further including an optical element in one of the optical paths for modifying the polarization of the radiation.

339. A system as claimed in claim 338, wherein said optical element is retardation plate.

340. A system as claimed in claim 339, wherein the retardation plate is zero order plate.

341. A system a claimed in claim 339, wherein the retardation plate is low order plate.

342. A system as claimed in claim 169, wherein the first optical path includes at least a common portion through which radiation travels to the reflector from the source and reflected radiation travels from the reflector to the combining means.

343. A system as claimed in claim 169, wherein said means for applying optical radiation from said source through the first and second optical paths includes a first beam splitter for splitting the radiation from the source along said first and second optical paths.

344. A system as claimed in claim 343, wherein said first beam splitter also functions to combine the reflections from the sample and the reflector.

345. A system as claimed in claim 343, further including a second beam splitter separate from said first beam splitter, said second beam splitter functioning to combine the reflections from the sample and the reflector.

346. A system as claimed in claim 169, wherein the reference optical reflector is a corner cube.

347. A system as claimed in claim 169, wherein said processing means includes an analog to digital converter.

348. A system as claimed in claim 169, further including a transimpedance amplifier for generating a voltage varying signal in response to the output of the combining means and supplying that signal to the demodulating means.

349. A system as claimed in claim 169, further including a means for generating a voltage varying signal in response to the output of the combining means and supplying that signal to the demodulating means.

350. A system as claimed in claim 169, wherein said processing means detects points of interest in the demodulated output.

351. A system as claimed in claim 169, wherein means for altering includes a means for moving said reference optical reflector.

352. A system as claimed in claim 351, wherein the reference optical reflector is moved at a velocity greater than 1 cm/sec.

353. A system as claimed in claim 351, wherein said means for moving the reference optical reflector is a resonantly driven actuator.

354. A system as claimed in claim 169, further including a camera positioned to measure radiation reflected from the sample to facilitate alignment.

355. A system as claimed in claim 169, wherein each of said first and second optical paths includes an optical fiber and wherein the velocity at which the relative length of the optical paths is altered is greater than 1 cm/sec and wherein said processing means includes an analog to digital converter.

356. A system as claimed in claim 355, wherein said means for applying optical radiation from said source through the first and second optical paths includes a beam splitter for splitting the radiation from the source along said first and second optical paths and wherein said beam splitter also functions to combine the reflections from the sample and the reflector.

357. A system as claimed in claim 356, further including an optical element in one of the optical paths for modifying the polarization of the radiation.

358. A system as claimed in claim 356, further including a means for generating a voltage varying signal in response to the output of the combining means and supplying that signal to the demodulating means.

359. A method as recited in claim 170, further including the step of laterally scanning the radiation in a transverse direction over the sample and wherein said processing step includes forming an image having at least two dimensions.

360. A method as claimed in claim 359, wherein said image is in the form of a tomographic image.

361. A method as claimed in claim 170, wherein the step of demodulating the detected output includes performing dynamic range compression.

362. The method as claimed in claim 361, wherein a logarithmic amplifier is utilized in performing the dynamic range compression.

363. A method as claimed in claim 170, further including the step of generating a visible beam of radiation to facilitate alignment.

364. A method as claimed in claim 170, wherein each of said first and second optical paths includes an optical fiber.

365. A method as claimed in claim 364, wherein at least one end of each optical fiber is angled polished.

366. A method as claimed in claim 365, wherein at least one end of each optical fiber includes an anti-reflection coating.

367. A method as claimed in claim 364, wherein the lengths of the fibers are substantially equal.

368. A method as claimed in claim 364, wherein said optical fibers are single mode optical fibers.

369. A method as claimed in claim 359, wherein said image has a longitudinal resolution of approximately 10 micrometers.

370. A method as claimed in claim 170, wherein said optical radiation has a coherence length of less than 10 micrometers.

371. A method as claimed in claim 170, further including the step of focusing radiation onto the reference reflector.

372. A method as claimed in claim 170, wherein the velocity at which the relative length of the optical paths are altered is greater than 1 cm/sec.

373. A method as claimed in claim 170, further including the step of modifying the polarization of the radiation in one of the optical paths.

374. A method as claimed in claim 373, wherein the polarization is modified using a retardation plate.

375. A method as claimed in claim 170, wherein a beam splitter is used to divide the radiation along the first and second optical paths and the same beam splitter is used to combine the reflections from the reflector and the sample.

376. A method as claimed in claim 170, wherein the processing step includes converting the detected output from an analog signal to a digital signal.

377. A method as claimed in claim 170, wherein each of said first and second optical paths includes an optical fiber and wherein the velocity at which the relative length of the optical paths is altered is greater than 1 cm/sec and wherein the processing step includes converting the detected output from an analog signal to a digital signal.

378. A method as claimed in claim 377, wherein a beam splitter is used to divide the radiation along the first and second optical paths and the same beam splitter is used to combine the reflections from the reflector and the sample.

379. A method as claimed in claim 378, further including the step of modifying the polarization of the radiation in one of the optical paths.

* * * * *